(12) United States Patent
Lewis et al.

(10) Patent No.: US 12,258,530 B2
(45) Date of Patent: Mar. 25, 2025

(54) ALKYLATED NAPHTHALENE COMPOSITIONS OBTAINED THROUGH BLENDING OR PROCESSING OF MONOALKYLATED AND DIALKYLATED NAPHTHALENE FRACTIONS

(71) Applicant: ExxonMobil Chemical Patents Inc., Baytown, TX (US)

(72) Inventors: Kyle G. Lewis, Houston, TX (US); Wenning W. Han, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 263 days.

(21) Appl. No.: 17/757,342

(22) PCT Filed: Dec. 16, 2020

(86) PCT No.: PCT/US2020/065385
§ 371 (c)(1),
(2) Date: Jun. 14, 2022

(87) PCT Pub. No.: WO2021/127028
PCT Pub. Date: Jun. 24, 2021

(65) Prior Publication Data
US 2023/0052422 A1    Feb. 16, 2023

Related U.S. Application Data

(60) Provisional application No. 62/951,392, filed on Dec. 20, 2019.

(30) Foreign Application Priority Data

Mar. 3, 2020   (EP) .................................. 20160557

(51) Int. Cl.
*C10M 105/06* (2006.01)
*C07C 7/04* (2006.01)
(Continued)

(52) U.S. Cl.
CPC ............. *C10M 105/06* (2013.01); *C07C 7/04* (2013.01); *C10M 177/00* (2013.01);
(Continued)

(58) Field of Classification Search
CPC ............. C10M 105/06; C10M 177/00; C10M 2203/065; C10M 2203/06; C10M 127/04;
(Continued)

(56) References Cited

U.S. PATENT DOCUMENTS 3,959,399 A    5/1976  Bridwell et al.
4,604,491 A    8/1986  Dressler et al.
(Continued)

FOREIGN PATENT DOCUMENTS

WO    2021/127028 A1    6/2021

OTHER PUBLICATIONS

Extended European Search Report received for European Patent Application No. 20160557.3, mailed on Aug. 17, 2020, 11 Pages.
(Continued)

*Primary Examiner* — Prem C Singh
*Assistant Examiner* — Francis C Campanell

(57) ABSTRACT

Alkylated naphthalene compositions are usually formed by reacting naphthalene with an electrophilic agent under acid-catalyzed conditions to afford a mixture of monoalkylated naphthalenes, dialkylated naphthalenes, and sometimes polyalkylated naphthalenes. Reaction conditions are usually chosen to change the product distribution for purposes of modifying lubricant properties such as viscosity or volatility. Rarely does the product distribution exceed 90 wt. % monoalkylated naphthalenes. Viscosity and volatility may alternately be modified by obtaining a first fraction enriched in monoalkylated naphthalenes and a second fraction enriched in dialkylated naphthalenes and combining the first fraction and the second fraction in a specified ratio to
(Continued)

produce a modified alkylated naphthalene composition having a targeted value of one of the viscosity or the volatility. The first fraction and the second fraction may be obtained by fractional distillation of a first alkylated naphthalene composition to afford an overhead fraction and a bottoms fraction.

9 Claims, 8 Drawing Sheets

(51) Int. Cl.
| | |
|---|---|
| *C10M 177/00* | (2006.01) |
| *C10N 20/02* | (2006.01) |
| *C10N 30/00* | (2006.01) |
| *C10N 30/02* | (2006.01) |
| *C10N 40/04* | (2006.01) |
| *C10N 40/25* | (2006.01) |
| *C10N 70/00* | (2006.01) |

(52) U.S. Cl.
CPC ... *C07C 2602/10* (2017.05); *C10M 2203/065* (2013.01); *C10N 2020/02* (2013.01); *C10N 2030/02* (2013.01); *C10N 2030/74* (2020.05); *C10N 2040/04* (2013.01); *C10N 2040/25* (2013.01); *C10N 2070/00* (2013.01)

(58) Field of Classification Search
CPC ........ C10M 143/00; C10M 2203/1025; C10M 2205/22; C10M 107/02; C07C 7/04; C07C 2602/10; C10N 2020/02; C10N 2030/02; C10N 2030/74; C10N 2040/04; C10N 2040/25; C10N 2070/00; C10N 2030/18
USPC ............................................................ 585/1
See application file for complete search history.

(56) References Cited

U.S. PATENT DOCUMENTS

| 5,177,284 | A | | 1/1993 | Le et al. |
|---|---|---|---|---|
| 5,191,135 | A | * | 3/1993 | Dwyer ...................... C07C 2/66 585/455 |
| 9,238,599 | B2 | | 1/2016 | Winsett |
| 2013/0150608 | A1 | | 6/2013 | Winsett et al. |
| 2014/0274838 | A1 | | 9/2014 | Cooper et al. |

OTHER PUBLICATIONS

Friedman, H. M. et al., (1969) "Alkylation of naphthalene with alkenes", The Journal of Organic Chemistry, vol. 34, No. 10, pp. 3211-3213.
International Preliminary Report on Patentability received for PCT Application No. PCT/US2020/065385, mailed on Jun. 30, 2022, 9 Pages.
International Search Report and Written Opinion received for PCT Application No. PCT/US2020/065385, mailed on Mar. 12, 2021, 13 Pages.

* cited by examiner

ALKYLATED NAPHTHALENE COMPOSITIONS OBTAINED THROUGH BLENDING OR PROCESSING OF MONOALKYLATED AND DIALKYLATED NAPHTHALENE FRACTIONS

PRIORITY

This application is a National Phase Application claiming priority to PCT Application Serial No. PCT/US2020/065385 filed Dec. 16, 2020, which claims priority to and the benefit of U.S. Provisional Application No. 62/951,392, filed Dec. 20, 2019, and European Patent Application No. 20160557.3 which was filed Mar. 3, 2020, the disclosures of which are incorporated herein by reference in their entireties.

FIELD

The present disclosure relates to lubricant compositions comprising alkylated naphthalenes.

BACKGROUND

Alkylated naphthalenes are a well-known class of compounds having lubricant properties, either by themselves or when blended in a formulated lubricant containing one or more additional base oils or additional components. Alkylated naphthalenes, particularly those bearing one or more alkyl groups having 6 carbon atoms or more, frequently demonstrate high oxidative and hydrolytic stability, low volatility, and good viscometric properties.

The carbon chain length and number of alkyl groups in alkylated naphthalenes can have significant impacts on their resulting lubricant properties, particularly the viscometric and volatility properties. As a particular example, dialkylated naphthalenes and higher polyalkylated naphthalenes may exhibit significantly poorer viscometric properties (higher viscosity) in comparison to the corresponding monoalkylated naphthalenes. Significant quantities of dialkylated and polyalkylated naphthalenes may be especially problematic with respect to the low-temperature viscometric behavior of alkylated naphthalenes.

Alkylated naphthalenes may be produced under electrophilic aromatic addition reaction conditions by contacting an alkene, an alkanol, or an alkyl halide with naphthalene or a naphthalene compound under acid catalysis, thereby introducing one or more alkyl groups to one or both of the fused phenyl rings of the naphthalene system. Typically, a distribution of monoalkylated, dialkylated and polyalkylated naphthalene rings, including various positional isomers thereof, may be produced under a given set of acid-catalyzed electrophilic aromatic addition reaction conditions. Dialkylated and sometimes polyalkylated naphthalene compounds may be produced in significant quantities through further alkylation of one or more initially formed monoalkylated naphthalenes, given the propensity of alkyl groups to promote aromatic ring activation. Indeed, it is often difficult to obtain greater than about 90 wt. % monoalkylated naphthalenes under electrophilic aromatic addition reaction conditions. Oftentimes, significantly higher quantities of dialkylated and other polyalkylated naphthalenes may form under a specified set of alkylation conditions.

Under a specified set of alkylation conditions, a particular product distribution of monoalkylated naphthalenes and dialkylated naphthalenes may result, such that the product distribution affords a set of known lubricant properties (e.g., particular viscometric properties and/or a particular volatility profile). The alkylation conditions may be varied (e.g., one or more of the molar ratio of naphthalene to electrophile, the acid catalyst, the reaction temperature, the reaction time, or a similar reaction parameter) to alter the product distribution obtained, thereby affording a different set of lubricant properties. Although a wide range of alkylated naphthalene compositions having considerable compositional and lubricant property variance may be obtained in the foregoing manner, it can be a considerable challenge to tailor the set of alkylation conditions to afford targeted lubricant properties that have not been produced previously. At the very least, it cannot be known a priori what product distribution a particular set of alkylation conditions will produce, much less the lubricant properties obtained therefrom.

Even if suitable alkylation conditions can be identified to directly synthesize alkylated naphthalenes having a targeted set of lubricant properties, parallel synthesis lines may be required when forming multiple grades of alkylated naphthalene lubricants at a single production facility. If a single synthesis line is used for synthesizing multiple grades of alkylated naphthalene lubricants, there may be significant production slowdowns when switching between production of different lubricant grades. As such, the number of alkylated naphthalene compositions produced at a given production site may be rather limited.

SUMMARY

In some embodiments, methods of the present disclosure may comprise: providing a first alkylated naphthalene composition comprising at least one monoalkylated naphthalene and at least one dialkylated naphthalene; obtaining a first fraction enriched in the at least one monoalkylated naphthalene and a second fraction enriched in the at least one dialkylated naphthalene; and combining a portion of the first fraction with a portion of the second fraction to obtain a modified alkylated naphthalene composition differing in composition from the first alkylated naphthalene composition and having one or more lubricant properties differing from the first alkylated naphthalene composition.

In some or other various embodiments, methods of the present disclosure may comprise: selecting a first alkylated naphthalene composition comprising at least one monoalkylated naphthalene and at least one dialkylated naphthalene, the at least one monoalkylated naphthalene and the at least one dialkylated naphthalene comprising a first alkyl group having a first carbon chain length, and the first alkylated naphthalene composition having a first viscosity and a first volatility; providing a second alkylated naphthalene composition comprising at least one monoalkylated naphthalene and at least one dialkylated naphthalene, the at least one monoalkylated naphthalene and the at least one dialkylated naphthalene comprising a second alkyl group having a second carbon chain length differing from the first carbon chain length; obtaining from the second alkylated naphthalene composition a first fraction enriched in the at least one monoalkylated naphthalene and a second fraction enriched in the at least one dialkylated naphthalene; selecting a value of one of the first viscosity or the first volatility to be matched with a modified alkylated naphthalene composition formed by combining a portion of the first fraction with a portion of the second fraction; and combining the portion of the first fraction with the portion of the second fraction to form the modified alkylated naphthalene composition, the portion of the first fraction and the portion of the second fraction being combined in an amount to provide the at least one monoalkylated naphthalene and the at least one dialkylated naphthalene in a ratio sufficient to substantially match the value of the first viscosity or the first volatility.

Additional embodiments may comprise: providing an alkylated naphthalene composition comprising at least one monoalkylated naphthalene and at least one dialkylated naphthalene; and distilling the alkylated naphthalene composition to obtain an overhead fraction at least partially enriched in the at least one monoalkylated naphthalene and at least partially depleted in the at least one dialkylated naphthalene, such that a ratio of the at least one monoalkylated naphthalene to the at least one dialkylated naphthalene in the overhead fraction is selected to target a specified viscosity or a specified volatility of the overhead fraction; wherein the overhead fraction comprises about 95 wt. % or above monoalkylated naphthalenes, and about 5 wt. % or below dialkylated naphthalenes.

In still other embodiments, alkylated naphthalene compositions of the present disclosure may comprise about 95 wt. % or above monoalkylated naphthalenes, and about 5 wt. % or lower dialkylated naphthalenes. Formulated lubricant compositions may be formed from the alkylated naphthalene compositions.

Other alkylated naphthalene compositions of the present disclosure may comprise about 13±1 wt. % $C_{16}$ monoalkylated naphthalene compounds, and about 87±1 wt. % $C_{16}$ dialkylated naphthalene compounds. The alkylated naphthalene compositions have each of the following properties: a kinematic viscosity at 100° C. of about 13 cSt or lower; a kinematic viscosity at 40° C. of about 114 cSt or lower; and a Noack volatility of about 2.5% or lower.

Still other alkylated naphthalene compositions may comprise about 30±1 wt. % $C_{16}$ monoalkylated naphthalene compounds, and about 70±1 wt. % $C_{16}$ dialkylated naphthalene compounds. The alkylated naphthalene compositions have each of the following properties: a kinematic viscosity at 100° C. of about 10 cSt or lower; a kinematic viscosity at 40° C. of about 84 cSt or lower; and a Noack volatility of about 5% or lower.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1A:
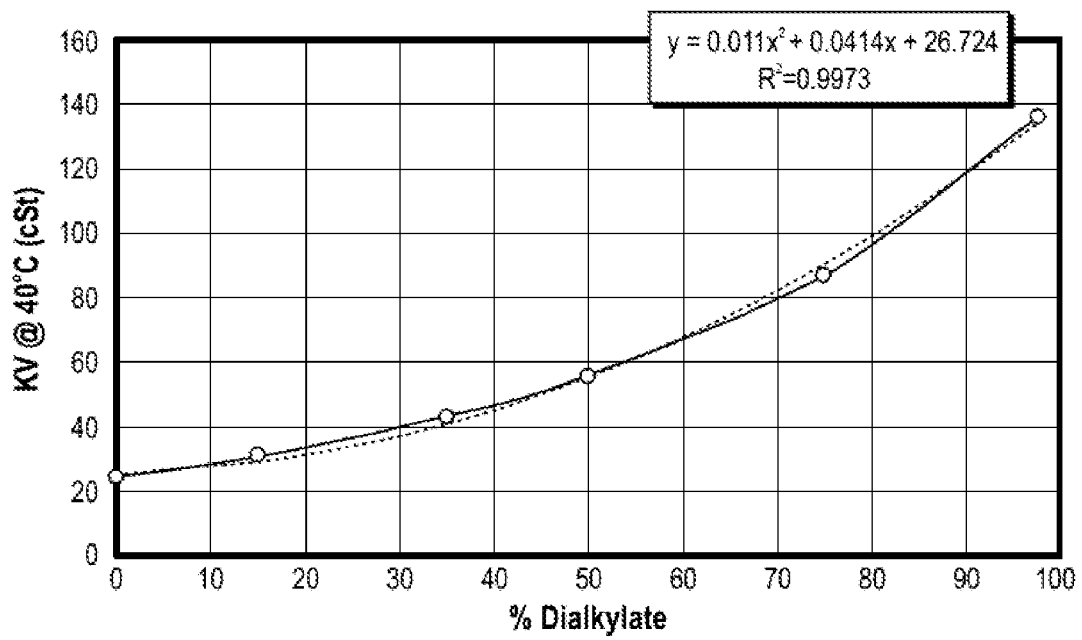
FIGS. 1A, 1B and 1C show plots of the kinematic viscosity at 40° C., the kinematic viscosity at 100° C., and the Noack volatility for blended $C_{16}$-alkylated naphthalene compositions versus the weight percentage of dialkylated naphthalenes present.

The present disclosure generally relates to alkylated naphthalenes and, more specifically, modified alkylated naphthalene compositions having specified lubricant properties that are obtainable from an in-common, previously synthesized alkylated naphthalene composition.

As discussed above, alkylated naphthalenes are well-known lubricant compounds. Alkylated naphthalenes are typically produced through electrophilic aromatic addition of an alkene, an alkanol, or an alkyl halide to naphthalene or a naphthalene compound to afford a range of monoalkylated and dialkylated naphthalene compounds. The ratio of monoalkylated to dialkylated naphthalenes obtained under particular alkylation (synthesis) conditions and the carbon chain length of the alkyl group may be varied to obtain specified lubricant properties. To produce an alkylated naphthalene composition having a desired set of lubricant properties via a direct synthesis, specified acid-catalyzed alkylation conditions that are known to afford particular lubricant properties may be employed. Should it be desired to form alkylated naphthalenes with a different product distribution that has not been previously obtained synthetically (e.g., to produce targeted lubricant properties), it can be a challenging proposition to identify suitable alkylation conditions for altering the product distribution in a predictable way to afford particular lubricant properties. Even if suitable alkylation conditions can be identified, there may be synthetic inefficiencies associated with producing multiple grades of alkylated naphthalenes having different lubricant properties at a single production facility.

The present disclosure addresses the foregoing challenges associated with forming alkylated naphthalene compositions having specified lubricant properties. In particular, the present disclosure allows multiple grades of alkylated naphthalene compositions having specified lubricant properties to be accessed through an in-common alkylated naphthalene composition or a limited number of in-common alkylated naphthalene compositions that is/are used to formulate a modified alkylated naphthalene composition having the specified lubricant properties. When more than one in-common alkylated naphthalene composition is used in conjunction with the disclosure herein, the alkylated naphthalene compositions may each feature an alkyl group having a different carbon chain length. Alkylated naphthalene compositions produced according to the present disclosure may also be referred to herein as modified alkylated naphthalene compositions. The modified alkylated naphthalene compositions of the present disclosure may be accessed by separating an in-common alkylated naphthalene composition having a set product distribution into a first fraction enriched in monoalkylated naphthalenes and a second fraction enriched in dialkylated naphthalenes (and polyalkylated naphthalenes, when present). In particular, an alkylated naphthalene composition may be separated by fractional distillation to afford an overhead fraction enriched in monoalkylated naphthalenes and a bottoms fraction enriched in dialkylated naphthalenes. The two fractions may then be recombined in variable amounts to provide a different product distribution of monoalkylated naphthalenes and dialkylated naphthalenes compared to that present in the base product distribution. The differing ratio of monoalkylated naphthalenes to dialkylated naphthalenes in the modified alkylated naphthalene compositions may alter the lubricant properties compared to those present in the in-common alkylated naphthalene composition. As such, modified alkylated naphthalene compositions having a continuous range of lubricant properties may be prepared from a single in-common alkylated naphthalene composition. The approach offered by the present disclosure is considerably more efficient than determining alkylation conditions needed to prepare a specified product distribution. In addition, the approach of the present disclosure may eliminate the process inefficiencies associated with running multiple production lines in parallel or changing the alkylated naphthalene composition form in a single production line.

In a variant of the disclosure herein, modified alkylated naphthalene compositions may be obtained by controlling distillation conditions to afford a specified ratio of monoalkylated naphthalenes to dialkylated naphthalenes in either an overhead fraction or a bottoms fraction, but without the overhead fraction and the bottoms fraction being recombined. Controlling the distillation conditions in this manner may similarly afford modified alkylated naphthalene compositions having tailored lubricant properties, as discussed further herein.

Surprisingly, the ratio at which monoalkylated naphthalenes and dialkylated naphthalenes are recombined with one another results in a predictable variance in the lubricant properties that are obtained. In particular, at least kinematic viscosity values and Noack volatility values measured for modified alkylated naphthalene compositions having a range ratios of monoalkylated naphthalenes to dialkylated naphthalenes may be fit to a regression function having a high $R^2$ value. The regression function may allow prediction of a lubricant property value for a modified alkylated naphthalene composition that has not yet been formulated or tested. Depending on the lubricant property, the data may be best fit with a polynomial regression function (at least a second-order polynomial) or an exponential regression function. Without being bound by theory, the polynomial or exponential fitting of the lubricant property data is believed to result from the logarithmic nature of the Arrhenius equation for mixtures [$\ln(X)=x_1\ln(A)+x_2\ln(B)$, wherein X is the average viscosity of the mixture, $x_1$ is the mole fraction of a first component, $x_2$ is the mole fraction of a second component, A is the viscosity of the first component, and B is the viscosity of the second component, and deviation from ideal solution behavior is reflective of the goodness of the curve fit]. Portions of the lubricant property data for modified alkylated naphthalenes having a low concentration of dialkylated naphthalenes (e.g., <10 wt. % dialkylated naphthalenes) may also be effectively fit with a linear regression function.

Modified alkylated naphthalene compositions of the present disclosure may be formulated (or obtained through selective distillation) at a ratio of monoalkylated naphthalenes to dialkylated naphthalenes to target a value for a particular lubricant property, such as kinematic viscosity or Noack volatility. The ratio of monoalkylated naphthalenes to dialkylated naphthalenes needed to produce the targeted value may be determined from the corresponding regression function. Once the ratio of monoalkylated naphthalenes to dialkylated naphthalenes has been determined from a first regression function associated with a first lubricant property, a predicted value for the other lubricant property may be predicted by inputting into a second regression function associated with the second lubricant property the ratio of monoalkylated naphthalenes to dialkylated naphthalenes. For examples, a ratio of monoalkylated naphthalenes to dialkylated naphthalenes may be selected to afford a predicted kinematic viscosity value, as determined from a kinematic viscosity regression function. The corresponding Noack volatility value may then be predicted at that ratio of monoalkylated naphthalenes to dialkylated naphthalenes by applying the corresponding regression function for Noack volatility. Once a particular lubricant property has been matched, the value of the other lubricant property follows by default at the particular ratio of monoalkylated naphthalenes to dialkylated naphthalenes needed for matching. That is, multiple lubricant properties are not independently variable when applying the concepts of the present disclosure.

By applying the concepts of the present disclosure in the foregoing manner, modified alkylated naphthalene compositions having a targeted profile of lubricant properties to be prepared. The targeted profile may include at least a particular combination of kinematic viscosity and Noack volatility. Particular combinations of kinematic viscosity and Noack volatility may be inaccessible in alkylated naphthalene compositions obtained via a direct synthesis under a specified set of alkylation conditions.

Moreover, the targeted profile of lubricant properties may also be chosen to match a particular lubricant property in an alkylated naphthalene composition having a second lubricant property that is insufficient or in need of enhancement. For example, a $C_{12}$-alkylated naphthalene composition obtained directly under a specified set of alkylation conditions may have good viscometric properties but possess a volatility that is too high for a particular application. The present disclosure allows monoalkylated naphthalenes and dialkylated naphthalenes comprising an alkyl group with a different carbon chain length to be recombined in a ratio suitable to meet the viscometric properties while simultaneously enhancing the volatility properties. In a non-limiting example, the viscometric properties of a $C_{12}$-alkylated naphthalene composition may be matched with a particular ratio of $C_{14}$-monoalkylated naphthalenes to $C_{14}$-dialkylated naphthalenes or a particular ratio of $C_{16}$-monoalykylated naphthalenes to $C_{16}$-dialkylated naphthalenes, in which case the volatility may be enhanced. In another non-limiting example, the volatility properties of an alkylated naphthalene composition may be matched with a particular ratio of monoalkylated naphthalenes to dialkylated naphthalenes comprising an alkyl group with a larger number of carbon atoms, thereby lowering the content of dialkylated naphthalenes compared to the alkylated naphthalene composition whose volatility is being matched. Lowering the content of dialkylated naphthalenes may be particularly advantageous with respect to improving the low-temperature viscometric properties of the modified alkylated naphthalene compositions formed in accordance with the present disclosure. Surprisingly, the present disclosure may allow modified alkylated naphthalene compositions having both enhanced viscometric properties and Noack volatility values to be realized. Improved low-temperature lubricant performance may also be achieved in some cases.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A" and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_n$" refers to hydrocarbon(s) or a hydrocarbyl group having n carbon atom(s) per molecule or group, wherein n is a positive integer. Such hydrocarbons or hydrocarbyl groups may be one or more of linear, branched, cyclic, acyclic, saturated, unsaturated, aliphatic, or aromatic.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. "Hydrocarbyl groups" may be optionally substituted, in which the term "optionally substituted" refers to replacement of at least one hydrogen atom or at least one carbon atom with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbyl groups include, but are not limited to, functional groups such as O, S, S=O, S(=O)$_2$, NO$_2$, F, Cl, Br, I, NR$_2$, OR, SeR, TeR, PR$_2$, AsR$_2$, SbR$_2$, SR, BR$_2$, SiR$_3$, GeR$_3$, SnR$_3$, PbR$_3$, where R is a hydrocarbyl group or H. Suitable hydrocarbyl groups may include alkyl, alkenyl, alkynyl, aryl, heteroaryl, cycloalkyl, cycloalkenyl, heterocyclyl, and the like, any of which may be optionally substituted.

The terms "saturated" or "saturated hydrocarbon" refer to a hydrocarbon or hydrocarbyl group in which all carbon atoms are bonded to four other atoms or bonded to three other atoms with one unfilled valence position thereon.

The terms "unsaturated" or "unsaturated hydrocarbon" refer to a hydrocarbon or hydrocarbyl group in which one or more carbon atoms are bonded to less than four other atoms, optionally with one unfilled valence position on the one or more carbon atoms.

The term "alkyl" refers to a hydrocarbyl group having no unsaturated carbon-carbon bonds, and which may be optionally substituted. Preferably, alkyl groups present within the modified alkylated naphthalene compositions disclosed herein are unsubstituted.

The term "alkenyl" refers to a hydrocarbyl group having a carbon-carbon double bond, and which may be optionally substituted. The terms "alkene" and "olefin" may be used synonymously herein. Similarly, the terms "alkenic" and "olefinic" may be used synonymously herein. Unless otherwise noted, all possible geometric and positional isomers are encompassed by these terms.

The term "alpha olefin" refers to a hydrocarbon compound having a terminal double bond. Preferably, the alpha olefin is a "linear alpha olefin" having a substantially unbranched alkyl group appended to the terminal double bond.

The terms "aromatic" and "aromatic hydrocarbon" refer to a hydrocarbon or hydrocarbyl group having a cyclic arrangement of conjugated pi-electrons that satisfy the Hückel rule. The term "aryl" is equivalent to the term "aromatic" as defined herein. The term "aryl" refers to both aromatic compounds and heteroaromatic compounds, either of which may be optionally substituted. Both mononuclear and polynuclear aromatic compounds are encompassed by these terms. Aromatic rings within a mononuclear or polynuclear aromatic compound may be fused or unfused.

The terms "linear," "linear hydrocarbon" and "linear alkyl group" refer to a hydrocarbon, hydrocarbyl or alkyl group having a continuous carbon chain without side chain branching, in which the continuous carbon chain may be optionally substituted with heteroatoms or heteroatom groups. Preferably, such groups are unsubstituted in the modified alkylated naphthalene compositions disclosed herein.

The terms "branch," "branched," "branched hydrocarbon" and "branched alkyl" refer to a hydrocarbon, hydrocarbyl group or alkyl group having a linear main carbon chain in which a hydrocarbyl side chain extends from the linear main carbon chain. Optional heteroatom substitution may be present in the linear main carbon chain or in the hydrocarbyl side chain. Preferably, branched alkyl groups are unsubstituted. Conversely, the term "unbranched" refers to a hydrocarbon, hydrocarbyl group or alkyl group having a linear main carbon chain without any hydrocarbyl side chain extending from the linear main carbon chain.

The term "alkylated naphthalene" refers to a bicyclic organic compound containing two fused phenyl rings that collectively bear at least one alkyl group. The at least one alkyl group may be located at any available valence position upon the two fused phenyl rings. A "monoalkylated naphthalene" refers to an alkylated naphthalene containing one alkyl group located at any open valence position. A "dialkylated naphthalene" refers to an alkylated naphthalene containing two alkyl groups located at any open valence position. A "polyalkylated naphthalene" refers to an alkylated naphthalene containing two or more alkyl groups located at any open valence position, preferably three or more alkyl groups located at any open valence position.

The term "overhead fraction" refers to any distillable fraction obtained during a fractional distillation. The term "bottoms fraction" refers to any non-distillable fraction obtained during a fractional distillation.

The term "enriched" refers to a substance containing a higher quantity of a specified component, as compared to a reference substance or a parent substance from which an enriched substance was prepared. The term "depleted" refers to a substance having a lower quantity of a specified component, as compared to a reference substance or a parent substance from which a depleted substance was prepared. In a particular instance, an enriched substance may comprise at least about 70 wt. % or above of a specified component.

Accordingly, methods of the present disclosure may comprise: providing a first alkylated naphthalene composition comprising at least one monoalkylated naphthalene and at least one dialkylated naphthalene; obtaining a first fraction enriched in the at least one monoalkylated naphthalene and a second fraction enriched in the at least one dialkylated naphthalene; and combining a portion of the first fraction with a portion of the second fraction to obtain a modified alkylated naphthalene composition differing in composition from the first alkylated naphthalene composition and having one or more lubricant properties differing from the first alkylated naphthalene composition.

Any alkylated naphthalene composition may be used in practicing the disclosure herein, provided that the alkylated naphthalene composition contains at least one monoalkylated naphthalene, at least one dialkylated naphthalene, and optionally at least one polyalkylated naphthalene. Any ratio of the at least one monoalkylated naphthalene to the at least one dialkylated naphthalene may be present in the alkylated naphthalene compositions suitable for use in the present disclosure. Preferably, the at least one monoalkylated naphthalene may be present in a greater amount than the at least one dialkylated naphthalene prior to obtaining the first fraction and the second fraction. In a non-limiting example, the alkylated naphthalene composition may be separated by fractional distillation or a similar separation technique capable of separating monoalkylated naphthalenes into a first fraction and dialkylated naphthalenes into a second fraction. When the first fraction and the second fraction are separated by fractional distillation of the first alkylated naphthalene composition, the first fraction may comprise an overhead fraction of the fractional distillation and the second fraction may comprise a bottoms fraction of the fractional distillation. The alkylated naphthalene composition may be sourced from an appropriate supplier or synthesized de novo in practicing the concepts of the present disclosure. Synthesis of the alkylated naphthalene composition, either de novo or when conducted by a supplier, may comprise reacting an olefin, an alkyl halide, an alkanol, or any combination thereof with naphthalene under acid-catalyzed conditions. Suitable acid catalysts are not considered to be particularly limited and may include, for example, mineral acids, Lewis acids, solid acid catalysts such as zeolites, or any combination thereof. Other alkylation conditions employed when synthesizing alkylated naphthalene compositions under acid-catalyzed conditions will be familiar to one having ordinary skill in the art.

Suitable fractional distillation conditions may vary based upon the alkylated naphthalene composition undergoing distillation and other various factors including, but not limited to the size of the distillation equipment, the distillation rate, the temperature/pressure balance, stripping gas flow rates (e.g., steam or nitrogen), and the like. In non-limiting examples, suitable conditions for distilling alkylated naphthalenes may include a temperature of at least about 350° F. (177° C.) and a pressure of about 200 mm Hg (26,665 Pa) or below. Further description of the conditions suitable for distilling alkylated naphthalenes, including conditions for steam distillation, are described in U.S. Patent Application Publication 2013/0150608, which is incorporated herein by reference in its entirety.

The at least one monoalkylated naphthalene and the at least one dialkylated naphthalene may comprise a $C_6$-$C_{20}$ alkyl group in particular alkylated naphthalene compositions suitable for use in the disclosure herein. Alkylated naphthalenes that may be present in the alkylated naphthalene compositions prior to separation into a first fraction and a second fraction may be represented by Structure 1 below,

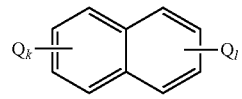

Structure 1 wherein each Q is an alkyl group, preferably a $C_6$-$C_{20}$ alkyl group, and k and l are integers representing the number of occurrences of Q on each fused phenyl ring. For monoalkylated naphthalenes, the sum of k+l equals 1, and for dialkylated naphthalenes, the sum of k+l equals 2. Either fused phenyl ring may be alkylated in a monoalkylated naphthalene, and either or both fused phenyl rings may be alkylated in a dialkylated naphthalene.

In more particular examples, the $C_6$-$C_{20}$ alkyl group may be derived from an alpha olefin, such that the alkylated naphthalenes may be represented by Structure 2,

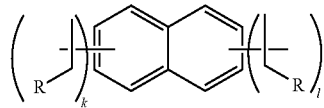

Structure 2 wherein R is a $C_4$-$C_{18}$ hydrocarbyl group, preferably an unbranched $C_4$-$C_{18}$ alkyl group, and k and l are defined as above. Examples of alpha olefins that may be suitably employed for forming alkylated naphthalenes for use in the disclosure herein include, for example, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene. Alpha olefins having an even number of carbon atoms (e.g., 1-hexene, 1-octene, 1-decene, and so on), may be particularly desirable alpha olefins due to their ready availability through ethylene oligomerization under Ziegler-type catalysis.

When alkylating naphthalene under acid-catalyzed alkylation conditions, alkylation may take place upon a terminal carbon atom or a non-terminal carbon atom of the electrophile. As will be appreciated by one having ordinary skill in the art, electrophilic aromatic addition of naphthalene may take place through a carbocation intermediate, which rearrange during the alkylation process to produce a more stable carbocation. Thus, in the case of an alpha olefin, a non-terminal carbon atom (e.g., C-2, C-3, etc.) may represent the point of attachment to the naphthalene ring system. Certain catalysts and alkylation conditions may be capable of promoting alkylation through C-1 of the alpha olefin, however.

Alkylated naphthalene compositions used in the present disclosure may be synthesized using a variety of alkylation conditions. Suitable alkylation conditions are known in the art and may vary based upon the acid catalyst used. Suitable reaction temperatures may range from about 0° C. to about 500° C., preferably from about 50° C. to about 250° C. Suitable pressures may range from about 0.2 atmospheres to about 250 atmospheres, preferably from about 5 atmospheres to about 100 atmospheres. Again, it is to be emphasized that any alkylated naphthalene composition and alkylation conditions used for production thereof may be suitable for use in the disclosure herein, provided that both monoalkylated naphthalenes and dialkylated naphthalenes are formed. It is to be further appreciated that alkylated naphthalene compositions comprising an alkyl group with a certain carbon chain length may sometimes be more advantageous for targeting a particular lubricant property, as explained in more detail hereinbelow.

In some instances, the first fraction may comprise about 50 wt. % or greater of the at least one monoalkylated naphthalene, and the second fraction may comprise about 50 wt. % or greater of the at least one dialkylated naphthalene, but lower amounts may be present in either fraction. In more particular examples, the first fraction may comprise about 95 wt. % or greater of the at least one monoalkylated naphthalene, and the second fraction may comprise about 80 wt. % or greater of the at least one dialkylated naphthalene. In a more specific example, the first fraction may comprise about 99 wt. % or greater of the at least one monoalkylated naphthalene, and the second fraction may comprise about 90 wt. % or greater of the at least one dialkylated naphthalene. It is also to be appreciated that the first fraction may comprise about 95 wt. % or greater or about 99 wt. % or greater of the least one monoalkylated naphthalene, independent of the amount of the at least one dialkylated naphthalene in the second fraction. Similarly, it is to be appreciated that the second fraction may comprise about 80 wt. % or greater or at least about 90 wt. % or greater of the at least one dialkylated naphthalene, independent of the amount of the at least one monoalkylated naphthalene in the first fraction. Although the amounts of monoalkylated naphthalenes and dialkylated naphthalenes may reside within the foregoing ranges, it is to be understood that as long as the amounts of monoalkylated naphthalenes and dialkylated naphthalenes in the first and second fractions are known, the concepts described herein may be applied to combine the at least one monoalkylated naphthalene and the at least one dialkylated naphthalene in a specified ratio to afford a desired lubricant property.

As described above, the first fraction and the second fraction may be combined in an amount sufficient to provide a specified ratio of the at least one monoalkylated naphthalene to the at least one dialkylated naphthalene to produce a given value for a lubricant property. Alternately, a specified ratio of the at least one monoalkylated naphthalene to the at least one dialkylated naphthalene may be obtained through distillation, without combining fractions in some instances. The lubricant property may include one or more of viscosity, volatility, or any combination thereof. The variance of a given lubricant property with respect to the ratio of monoalkylated naphthalenes to dialkylated naphthalenes may be established by preparing samples having known ratios of monoalkylated naphthalenes to dialkylated naphthalenes and determining a value of the given lubricant property for each sample using a suitable measurement technique. A calibration curve, regression function or lookup table may then be constructed using the values of the lubricant property for the known samples. The value of the lubricant property for a modified alkylated naphthalene composition having a ratio of monoalkylated naphthalenes to dialkylated naphthalenes differing from the known samples may then be determined by consulting the calibration curve, regression function or lookup table. The regression function may comprise a least squares fit of the lubricant property data, such as an exponential function, a polynomial function, and/or a linear function. The particular lubricant property and the breadth of the range of ratios of monoalkylated naphthalenes to dialkylated naphthalenes being measured may determine which least squares fitting protocol is most appropriate.

The calibration curves, regression functions, and/or lookup tables may be used to determine whether a targeted value for a given lubricant property may be attained for a particular type of alkylated naphthalene or a ratio of monoalkylated naphthalenes to dialkylated naphthalenes obtained therefrom. Alkylated naphthalenes having certain alkyl group carbon chain lengths, for example, may be incapable of providing a targeted value of a given lubricant property at any ratio of monoalkylated naphthalenes to dialkylated naphthalenes. If no ratio of monoalkylated naphthalenes to dialkylated naphthalenes is capable of producing a targeted value for a given lubricant property, one may select monoalkylated naphthalenes and dialkylated naphthalenes having a different carbon chain length and determining if combining those monoalkylated naphthalenes and dialkylated naphthalenes may produce the lubricant property at a specified ratio. Thus, it will be appreciated that multiple calibration curves, regression functions, and/or lookup tables may be used in conjunction with the disclosure herein to identify an alkylated naphthalene composition suitable for meeting a given lubricant property. The multiple calibration curves, regression functions, and/or lookup tables may be prepared for alkylated naphthalene compositions having an alkyl group with any carbon chain length of interest, some of which may be more optimal than others for producing the given lubricant property. For example, a given carbon chain length may satisfactorily produce a first lubricant property but be insufficient to produce a second lubricant property. As a non-limiting example, alkylated naphthalenes comprising an alkyl group with a particular carbon chain length may lead to a satisfactory kinematic viscosity but insufficient volatility. Conversely, a carbon chain length that affords satisfactory volatility may lead to poor viscometric properties. In both cases, alkylated naphthalenes comprising an alkyl group with a different carbon chain length may be selected to afford satisfactory values for both lubricant properties. In some instances, modified alkylated naphthalene compositions of the present disclosure may comprise alkyl groups having a single carbon chain length.

Accordingly, methods of the present disclosure may further comprise selecting a targeted value for one of the one or more lubricant properties, and determining an amount of the first fraction and an amount of the second fraction needed to provide a ratio of the least one monoalkylated naphthalene to the at least one dialkylated naphthalene to produce the targeted value of the lubricant property. Once the ratio of the at least one monoalkylated naphthalene to the at least one dialkylated naphthalene has been selected to produce a targeted value for a first lubricant property (e.g., kinematic viscosity), the value for a second lubricant property (e.g., Noack volatility) follows by default. As mentioned above, alkylated naphthalenes comprising an alkyl group with a different carbon chain length may be employed if the value for the second lubricant property is not within an acceptable range. As such, methods of the present disclosure may comprise selecting a carbon chain length for an alkyl group comprising the at least one monoalkylated naphthalene and the at least one dialkylated naphthalene to meet the targeted value when the first fraction and the second fraction are combined. In some cases, one may establish tolerance ranges for each lubricant property and a targeted value within each tolerance range and determine a ratio of monoalkylated naphthalenes to dialkylated naphthalenes and a carbon chain length thereof to afford a minimized variance from both targeted values. Thus, in some cases, it may not be possible to realize targeted values for two different lubricant properties simultaneously, but it may be possible to reach acceptable values within the tolerance ranges or one value reaching the targeted value for one lubricant property and the other value residing within the tolerance range for the other lubricant property. In establishing the targeted values, the ratio of the at least one monoalkylated naphthalene to the at least one dialkylated naphthalene may vary to some degree from an idealized value obtained from the calibration curves. In particular examples, the amount of the monoalkylated naphthalenes and the amount of the dialkylated naphthalenes may vary by ±1 wt. % over idealize values obtained from the calibration curves.

As discussed above, alkylated naphthalene lubricants are usually synthesized such that a particular ratio of monoalkylated naphthalenes to dialkylated naphthalenes results under the reaction conditions directly to afford a specified value for a first lubricant property (e.g., viscosity or volatility). In some cases, alkylated naphthalene lubricants obtained by a direct synthesis may have an unacceptable value for a second lubricant property (e.g., the other of viscosity of volatility). Direct syntheses have no way of addressing this issue, short of developing new synthetic conditions to change the ratio of monoalkylated naphthalenes to dialkylated naphthalenes, altering the carbon chain length employed, and/or blending with another alkylated naphthalene composition. In any event, it can be difficult to adjust the ratio of monoalkylated naphthalenes to dialkylated naphthalenes sufficiently. The present disclosure may alleviate this issue by allowing ready alteration of the carbon chain length within the monoalkylated naphthalenes and dialkylated naphthalenes to determine the impacts on the lubricant properties. More specifically, the present disclosure may allow matching of a given lubricant property for a first alkylated naphthalene composition comprising a first alkyl group with a first carbon chain length using a second alkylated naphthalene composition comprising a second alkyl group with a second carbon chain length different from the first carbon chain length.

Accordingly, methods for matching a lubricant property of an alkylated naphthalene composition with a modified alkylated naphthalene composition comprising an alkyl group with a different carbon chain length may comprise: selecting a first alkylated naphthalene composition comprising at least one monoalkylated naphthalene and at least one dialkylated naphthalene, the at least one monoalkylated naphthalene and the at least one dialkylated naphthalene comprising a first alkyl group having a first carbon chain length, and the first alkylated naphthalene composition having a first viscosity and a first volatility; providing a second alkylated naphthalene composition comprising at least one monoalkylated naphthalene and at least one dialkylated naphthalene, the at least one monoalkylated naphthalene and the at least one dialkylated naphthalene comprising a second alkyl group having a second carbon chain length differing from the first carbon chain length; obtaining from the second alkylated naphthalene composition a first fraction enriched in the at least one monoalkylated naphthalene and a second fraction enriched in the at least one dialkylated naphthalene; selecting a value of one of the first viscosity or the first volatility to be matched with a modified alkylated naphthalene composition formed by combining a portion of the first fraction with a portion of the second fraction obtained from the second alkylated naphthalene composition; and combining the portion of the first fraction with the portion of the second fraction to form the modified alkylated naphthalene composition, the portion of the first fraction and the portion of the second fraction being combined in an amount to provide the at least one monoalkylated naphthalene and the at least one dialkylated naphthalene in a ratio sufficient to substantially match the value of the first viscosity or the first volatility.

As discussed above, subdivision of the second alkylated naphthalene composition into the first fraction and the second fraction may take place by fractional distillation, such that the first fraction is enriched in the at least one monoalkylated naphthalene, and the second fraction is enriched in the at least one dialkylated naphthalene. Suitable fractional distillation conditions, amounts of monoalkylated naphthalene in the first fraction, and dialkylated naphthalene in the second fraction are discussed in more detail above and are fully applicable when the present disclosure is employed for matching a lubricant property of a first alkylated naphthalene composition.

Matching of the value of a lubricant property for an alkylated naphthalene composition with a modified alkylated naphthalene composition may enhance the value of a second lubricant property. Specifically, the modified alkylated naphthalene compositions produced according to the disclosure herein may have a lower viscosity or a higher volatility, depending upon which lubricant property is chosen for matching. For example, if the value of the first viscosity is selected for matching, the volatility of the modified alkylated naphthalene composition may be decreased, and if the value of the first volatility is selected for matching, the viscosity of the modified alkylated naphthalene composition is decreased.

Embodiments disclosed herein include:

A. Methods for formulating alkylated naphthalene compositions. The methods comprise: providing a first alkylated naphthalene composition comprising at least one monoalkylated naphthalene and at least one dialkylated naphthalene; obtaining a first fraction enriched in the at least one monoalkylated naphthalene and a second fraction enriched in the at least one dialkylated naphthalene; and combining a portion of the first fraction with a portion of the second fraction to obtain a modified alkylated naphthalene composition differing in composition from the first alkylated naphthalene composition and having one or more lubricant properties differing from the first alkylated naphthalene composition.

B. Methods for formulating alkylated naphthalene compositions to match one or more properties of a selected alkylated naphthalene composition. The methods comprise: selecting a first alkylated naphthalene composition comprising at least one monoalkylated naphthalene and at least one dialkylated naphthalene, the at least one monoalkylated naphthalene and the at least one dialkylated naphthalene comprising a first alkyl group having a first carbon chain length, and the first alkylated naphthalene composition having a first viscosity and a first volatility; providing a second alkylated naphthalene composition comprising at least one monoalkylated naphthalene and at least one dialkylated naphthalene, the at least one monoalkylated naphthalene and the at least one dialkylated naphthalene comprising a second alkyl group having a second carbon chain length differing from the first carbon chain length; obtaining from the second alkylated naphthalene composition a first fraction enriched in the at least one monoalkylated naphthalene and a second fraction enriched in the at least one dialkylated naphthalene; selecting a value of one of the first viscosity or the first volatility to be matched with a modified alkylated naphthalene composition formed by combining a portion of the first fraction with a portion of the second fraction; and combining the portion of the first fraction with the portion of the second fraction to form the modified alkylated naphthalene composition, the portion of the first fraction and the portion of the second fraction being combined in an amount to provide the at least one monoalkylated naphthalene and the at least one dialkylated naphthalene in a ratio sufficient to substantially match the value of the first viscosity or the first volatility.

C. Methods for obtaining alkylated naphthalene compositions by distillation. The methods comprise: providing an alkylated naphthalene composition comprising at least one monoalkylated naphthalene and at least one dialkylated naphthalene; and distilling the alkylated naphthalene composition to obtain an overhead fraction at least partially enriched in the at least one monoalkylated naphthalene and at least partially depleted in the at least one dialkylated naphthalene, a ratio of the at least one monoalkylated naphthalene to the at least one dialkylated naphthalene in the overhead fraction being selected to target a specified viscosity or a specified volatility of the overhead fraction; wherein the overhead fraction comprises about 95 wt. % or above monoalkylated naphthalenes, and about 5 wt. % or below dialkylated naphthalenes.

D. Alkylated naphthalene compositions containing high amounts of monoalkylated naphthalenes. The compositions comprise: about 95 wt. % or above monoalkylated naphthalenes; and about 5 wt. % or below dialkylated naphthalenes.

E. Alkylated naphthalene compositions containing high amounts of dialkylated naphthalenes and having a Noack volatility of about 4.5% or lower. The compositions comprise: about 13±1 wt. % $C_{16}$ monoalkylated naphthalene compounds; and about 87±1 wt. % $C_{16}$ dialkylated naphthalene compounds; wherein the alkylated naphthalene composition has each of the following properties: a kinematic viscosity at 100° C. of about 13 cSt or lower; a kinematic viscosity at 40° C. of about 114 cSt or lower; and a Noack volatility of about 2.5% or lower.

F. Alkylated naphthalene compositions containing high amounts of dialkylated naphthalenes and having a Noack volatility of about 2% or lower. The compositions comprise: about 30±1 wt. % $C_{16}$ monoalkylated naphthalene compounds; and about 70±1 wt. % $C_{16}$ dialkylated naphthalene compounds; wherein the alkylated naphthalene composition has each of the following properties: a kinematic viscosity at 100° C. of about 10 cSt or lower; a kinematic viscosity at 40° C. of about 84 cSt or lower; and a Noack volatility of about 5% or lower.

G. Formulated lubricant compositions comprising monoalkylated naphthalenes and dialkylated naphthalenes, wherein a ratio of monoalkylated naphthalenes to dialkylated naphthalenes is chosen to provide a specified property.

Each of embodiments A-G may have one or more of the following additional elements in any combination:

Element 1: wherein the first fraction and the second fraction are obtained by fractional distillation of the first alkylated naphthalene composition, and the first fraction comprises an overhead fraction of the fractional distillation and the second fraction comprises a bottoms fraction of the fractional distillation.

Element 2: wherein providing the alkylated naphthalene composition comprises reacting an olefin, an alkyl halide, an alkanol, or any combination thereof with naphthalene under acid-catalyzed reaction conditions.

Element 3: wherein the at least one monoalkylated naphthalene and the at least one dialkylated naphthalene comprise a $C_6$-$C_{20}$ alkyl group.

Element 4: wherein the olefin comprises an alpha olefin.

Element 5: wherein the one or more lubricant properties comprise one or more of viscosity, volatility, or any combination thereof.

Element 6: wherein the second fraction further comprises at least one polyalkylated naphthalene.

Element 7: wherein the first fraction comprises about 95 wt. % or greater of the at least one monoalkylated naphthalene and the second fraction comprises about 80 wt. % or greater of the at least one dialkylated naphthalene.

Element 8: wherein the first fraction comprises about 99 wt. % or greater of the at least one monoalkylated naphthalene and the second fraction comprises about 90 wt. % or greater of the at least one dialkylated naphthalene.

Element 9: wherein the method further comprises selecting a targeted value for one of the one or more lubricant properties; and determining an amount of the first fraction and an amount of the second fraction needed to provide a ratio of the at least one monoalkylated naphthalene to the at least one dialkylated naphthalene to produce the targeted value.

Element 10: wherein the ratio of the at least one monoalkylated naphthalene to the at least one dialkylated naphthalene is determined from a calibration curve or a regression function.

Element 11: wherein the method further comprises selecting a carbon chain length for an alkyl group comprising the at least one monoalkylated naphthalene and the at least one dialkylated naphthalene to meet the targeted value when the first fraction and the second fraction are combined.

Element 12: wherein the first fraction and the second fraction are obtained by fractional distillation of the second alkylated naphthalene composition, and the first fraction comprises an overhead fraction of the fractional distillation and the second fraction comprises a bottoms fraction of the fractional distillation.

Element 13: wherein if the value of the first viscosity is selected for matching, the volatility of the modified alkylated naphthalene composition is decreased relative to the first alkylated naphthalene composition, and if the value of the first volatility is selected for matching, the viscosity of the modified alkylated naphthalene composition is decreased relative to the first alkylated naphthalene composition.

Element 14: wherein the second carbon chain length of the second alkyl group is longer than the first carbon chain length of the first alkyl group.

Element 15: wherein the first fraction comprises about 95 wt. % or greater of the at least one monoalkylated naphthalene and the second fraction comprises about 80 wt. % or greater of the at least one dialkylated naphthalene.

Element 16: wherein the first fraction comprises about 99 wt. % or greater of the at least one monoalkylated naphthalene and the second fraction comprises about 90 wt. % or greater of the at least one dialkylated naphthalene.

Element 17: wherein the ratio of the at least one monoalkylated naphthalene to the at least one dialkylated naphthalene is determined from a calibration curve or a regression function.

Element 18: selecting the second carbon chain length of the second alkyl group such that the value of the first viscosity or the first volatility is matched once the first fraction and the second fraction are combined.

Element 19: wherein the monoalkylated naphthalenes and the dialkylated naphthalenes comprise alkyl groups having a single carbon chain size.

Element 20: wherein the alkyl groups are $C_{16}$ alkyl groups.

Element 21: wherein the alkylated naphthalene composition has one or more of the following properties: a kinematic viscosity at 100° C. of about 4.6 cSt or lower; a Noack volatility of about 11.6% or lower; and a Brookfield viscosity at −40° C. of about 30,000 cP or lower.

Element 22: wherein the alkylated naphthalene composition has each of the following properties: a kinematic viscosity at 100° C. of about 4.6 cSt or lower; a Noack volatility of about 11.6% or lower; and a Brookfield viscosity at −40° C. of about 30,000 cP or lower.

Element 23: wherein the alkylated naphthalene composition comprises about 13±1 wt. % $C_{16}$ monoalkylated naphthalene compounds; and about 87±1 wt. % $C_{16}$ dialkylated naphthalene compounds; wherein the alkylated naphthalene composition has each of the following properties: a kinematic viscosity at 100° C. of about 13 cSt or lower; a kinematic viscosity at 40° C. of about 114 cSt or lower; and a Noack volatility of about 2.5% or lower.

Element 24: wherein the alkylated naphthalene composition comprises about 30±1 wt. % $C_{16}$ monoalkylated naphthalene compounds; and about 70±1 wt. % $C_{16}$ dialkylated naphthalene compounds; wherein the alkylated naphthalene composition has each of the following properties: a kinematic viscosity at 100° C. of about 10 cSt or lower; a kinematic viscosity at 40° C. of about 84 cSt or lower; and a Noack volatility of about 5% or lower.

Element 25: wherein the formulated lubricant composition comprises about 10 wt. % or less of the alkylated naphthalene composition.

Element 26: wherein the formulated lubricant composition comprises an engine oil, an automotive gear oil, or an industrial gear oil.

By way of non-limiting example, exemplary combinations applicable to A include, but are not limited to, 1 and 2; 1 and 3; 1 and 5; 1 and 6; 1 and 7; 1 and 8; 1 and 9; 1 and 10; 1 and 11; 1 and 19; 1 and 20; 1 and 21; 1 and 22; 1 and 23; 1 and 24; 2 and 3; 2 and 4; 2 and 5; 2 and 6; 2 and 7; 2 and 8; 2 and 9; 2 and 10; 2 and 11; 2 and 19; 2 and 20; 2 and 21; 2 and 22; 2 and 23; 2 and 24; 3 and 4; 3 and 5; 3 and 6; 3 and 7; 3 and 8; 3 and 9; 3 and 10; 3 and 11; 3 and 19; 3 and 20; 3 and 21; 3 and 22; 3 and 23; 3 and 24; 5 and 6; 5 and 7; 5 and 8; 5 and 9; 5 and 10; 5 and 11; 5 and 19; 5 and 20; 5 and 21; 5 and 22; 5 and 23; 5 and 24; 7 or 8 and 9; 7 or 8 and 10; 7 or 8 and 11; 9 and 10; 9 and 11; 9 and 21; 9 and 22; 9 and 23; 9 and 24; 10 and 11; 10 and 21; 10 and 22; 10 and 23; and 10 and 24. Exemplary combinations applicable to B include, but are not limited to, 12 and 13; 12 and 14; 12 and 15; 12 and 16; 12 and 17; 12 and 18; 13 and 14; 13 and 15; 13 and 16; 13 and 17; 13 and 18; 14 and 15; 14 and 16; 14 and 17; 14 and 18; 15-17; 15, 16 and 18; and 17 and 18. Exemplary combinations applicable to D include, but are not limited to, 19 and 20; 19 and 21; 19 and 22; 20 and 21; and 21 and 22.

To facilitate a better understanding of the disclosure herein, the following examples of preferred or representative embodiments are given. In no way should the following examples be read to limit, or to define, the scope of the invention.

EXAMPLES

Example 1: Naphthalene was alkylated with 1-octene, 1-dodecene, or 1-hexadecene under acid-catalyzed conditions to produce alkylated naphthalene (AN) compositions specified in Table 1. The acid catalyst in each case was USY-H, the reaction temperature was 200-210° C., and the reaction time was 150 minutes. The mole ratio of the electrophile to naphthalene was 1.15:1 in each case.

TABLE 1

| Product Description | Electrophile | Wt. % Monoalkylated Naphthalenes | Wt. % Dialkylated Naphthalenes |
|---|---|---|---|
| $C_{16}$ AN | 1-hexadecene | 90 | 10 |
| $C_{12}$ AN | 1-dodecene | 86 | 14 |
| $C_8$ AN | 1-octene | 77 | 23 |

The above product mixtures were obtained after fraction distillation to remove unreacted electrophile and unreacted naphthalene. The remaining residue was subjected to further fractional distillation to afford an overhead fraction comprising predominantly monoalkylated naphthalenes (MAN) and a bottoms fraction comprising predominantly dialkylated naphthalenes (DAN). The composition of each overhead and bottoms fraction is specified in Table 2 below.

TABLE 2

| | Overhead Fraction | | Bottoms Fraction | |
|---|---|---|---|---|
| Product Description | Wt. % MAN | Wt. % DAN | Wt. % MAN | Wt. % DAN |
| $C_{16}$ AN | 99.8 | 0.2 | 2.2 | 97.8 |
| $C_{12}$ AN | 100.0 | 0.0 | 17.1 | 82.9 |
| $C_8$ AN | 100.0 | 0.0 | 4.3 | 95.7 |

The fractions obtained as above were then blended in various ratios to afford modified alkylated naphthalene compositions having a product distribution differing from that of the original alkylated naphthalene composition. Overhead fractions and bottoms fractions obtained from the same original alkylated naphthalene composition (i.e., overhead fractions and bottoms fractions having the same alkyl group carbon count) were combined in this example. The product distributions obtained following blending of the overhead fractions and the bottoms fractions in various ratios are specified in Tables 3-5 below for $C_{16}$ alkylated naphthalenes, $C_{12}$ alkylated naphthalenes, and $C_8$ alkylated naphthalenes, respectively. The modified alkylated naphthalene compositions formed through blending were then analyzed to determine their kinematic viscosity values at 40° C. and 100° C. by ASTMD5800, their viscosity indices by ASTM D2270, and their Noack volatility values by ASTM D445. The modified alkylated naphthalene compositions with the highest percentages of monoalkylated naphthalenes or dialkylated naphthalenes in Tables 3-5 below represent the as-obtained overhead fraction (monoalkylated naphthalenes) and the as-obtained bottoms fraction (dialkylated naphthalenes), without blending with the other fraction.

TABLE 3

$C_{16}$ Alkylated Naphthalene Compositions

| Entry | Wt. % Monoalkylated Naphthalenes | Wt. % Dialkylated Naphthalenes | Kinematic Viscosity @ 40° C. | Kinematic Viscosity @ 100° C. | Viscosity Index | Noack Volatility |
|---|---|---|---|---|---|---|
| 1a | 2.25 | 97.75 | 137.4 | 14.66 | 106 | 0.63 |
| 2a | 25 | 75 | 88.0 | 10.72 | 106 | 3.68 |
| 3a | 50 | 50 | 56.2 | 7.77 | 102 | 6.57 |
| 4a | 65 | 35 | 43.5 | 6.47 | 97 | 8.37 |
| 5a | 85 | 15 | 31.4 | 5.13 | 89 | 10.38 |
| 6a | 100 | 0 | 25.0 | 4.36 | 67 | 11.47 |

TABLE 4

$C_{12}$ Alkylated Naphthalene Compositions

| Entry | Wt. % Monoalkylated Naphthalenes | Wt. % Dialkylated Naphthalenes | Kinematic Viscosity @ 40° C. | Kinematic Viscosity @ 100° C. | Viscosity Index | Noack Volatility |
|---|---|---|---|---|---|---|
| 1b | 17.3 | 82.7 | 70.13 | 8.45 | 90 | 6.16 |
| 2b | 48.6 | 51.4 | 37.28 | 5.59 | 82 | 19.56 |
| 3b | 63.7 | 36.3 | 28.55 | 4.62 | 59 | 25.52 |
| 4b | 85.6 | 14.4 | 20.03 | 3.61 | 20 | 34.38 |
| 5b | 99.9 | 0.1 | 16.06 | 3.12 | 13 | 37.44 |

TABLE 5

$C_8$ Alkylated Naphthalene Compositions

| Entry | Wt. % Monoalkylated Naphthalenes | Wt. % Dialkylated Naphthalenes | Kinematic Viscosity @ 40° C. | Kinematic Viscosity @ 100° C. | Viscosity Index | Noack Volatility |
|---|---|---|---|---|---|---|
| 1c | 4.3 | 95.7 | 55.16 | 6.24 | 32 | 20.35 |
| 2c | 25.7 | 74.3 | 33.70 | 4.55 | −10 | 36.23 |
| 3c | 50.3 | 49.7 | 20.05 | 3.39 | −24 | 56.25 |
| 4c | 65.2 | 34.8 | 15.14 | 2.86 | −28 | 71.95 |
| 5c | 84.4 | 15.6 | 10.76 | 2.32 | −30 | 100 |

Figure 1B:
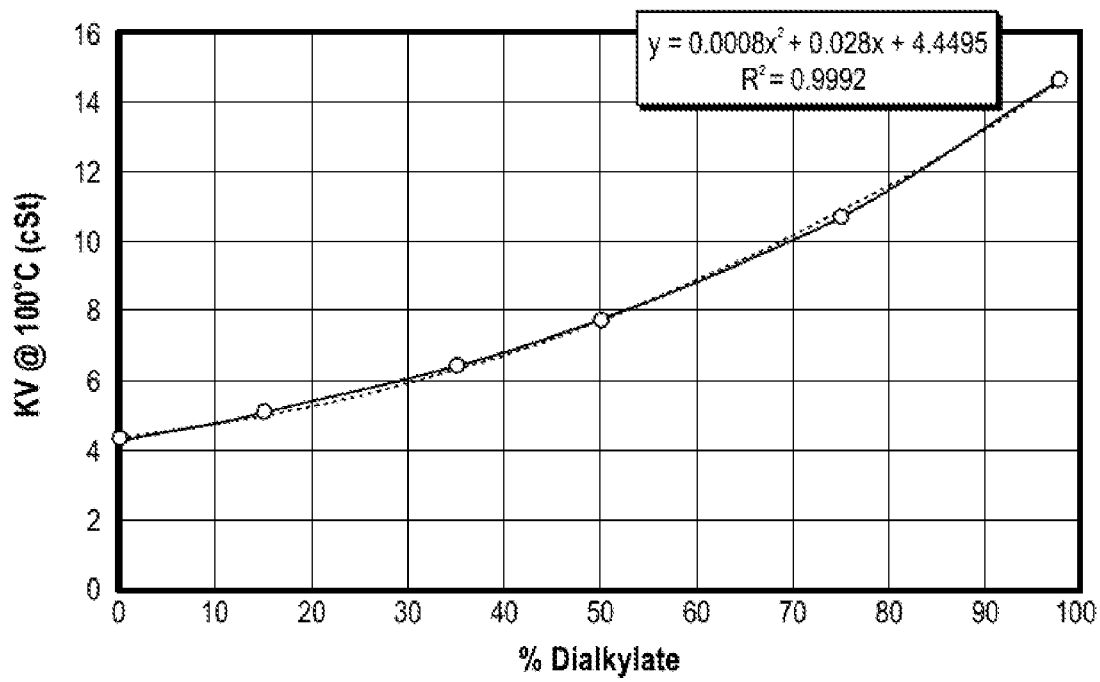
Figure 1C:
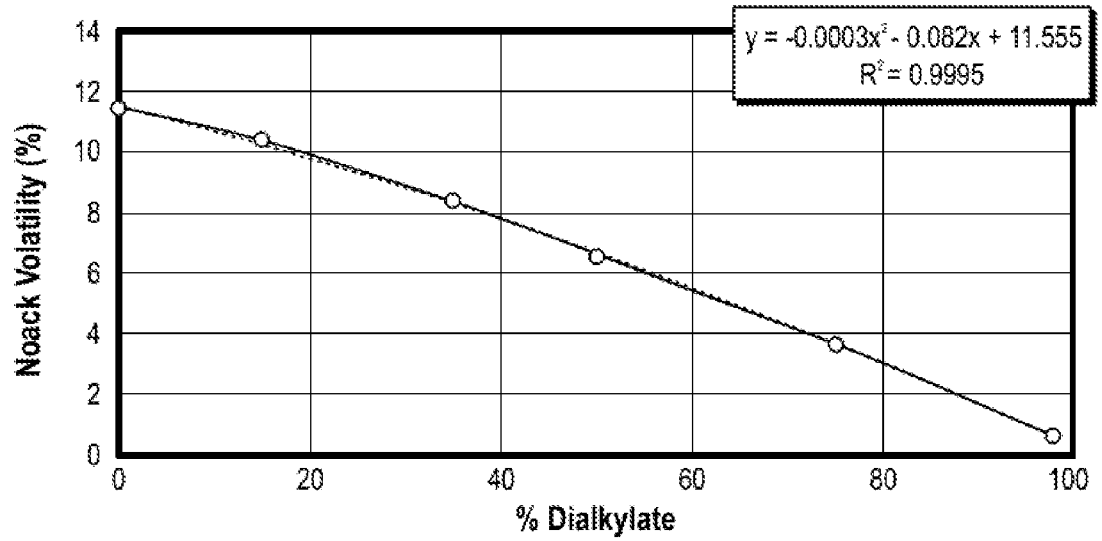
Figure 2A:
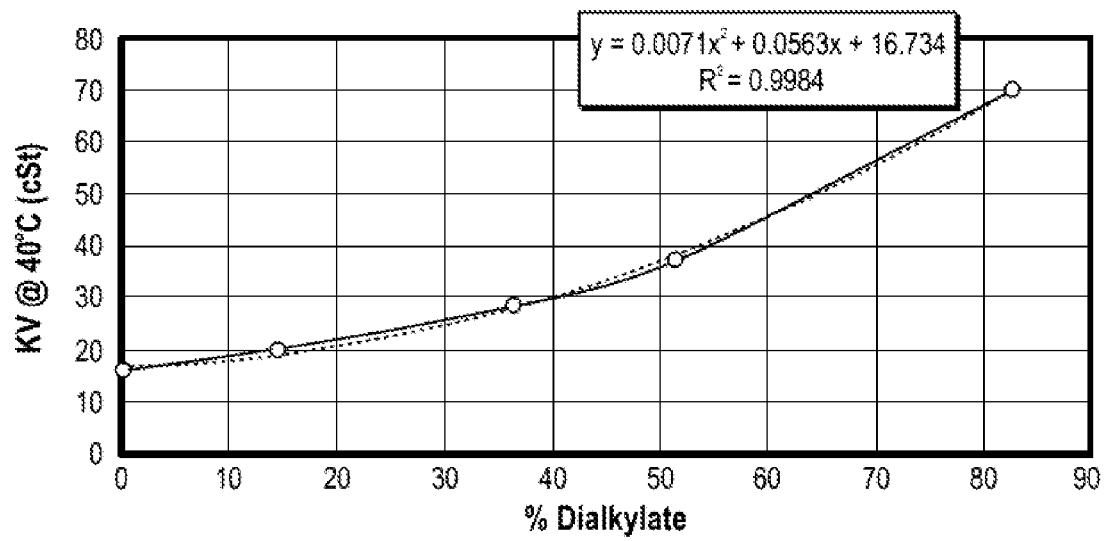
FIGS. 2A, 2B and 2C show plots of the kinematic viscosity at 40° C., the kinematic viscosity at 100° C., and the Noack volatility for blended $C_{12}$-alkylated naphthalene compositions versus the weight percentage of dialkylated naphthalenes present.
Figure 2B:
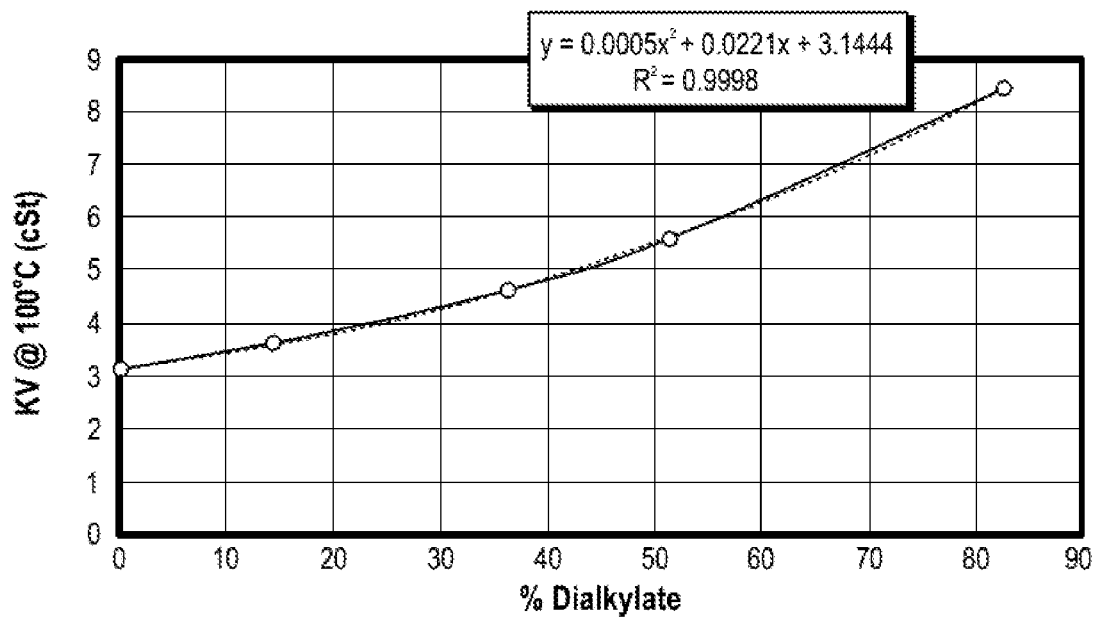
Figure 2C:
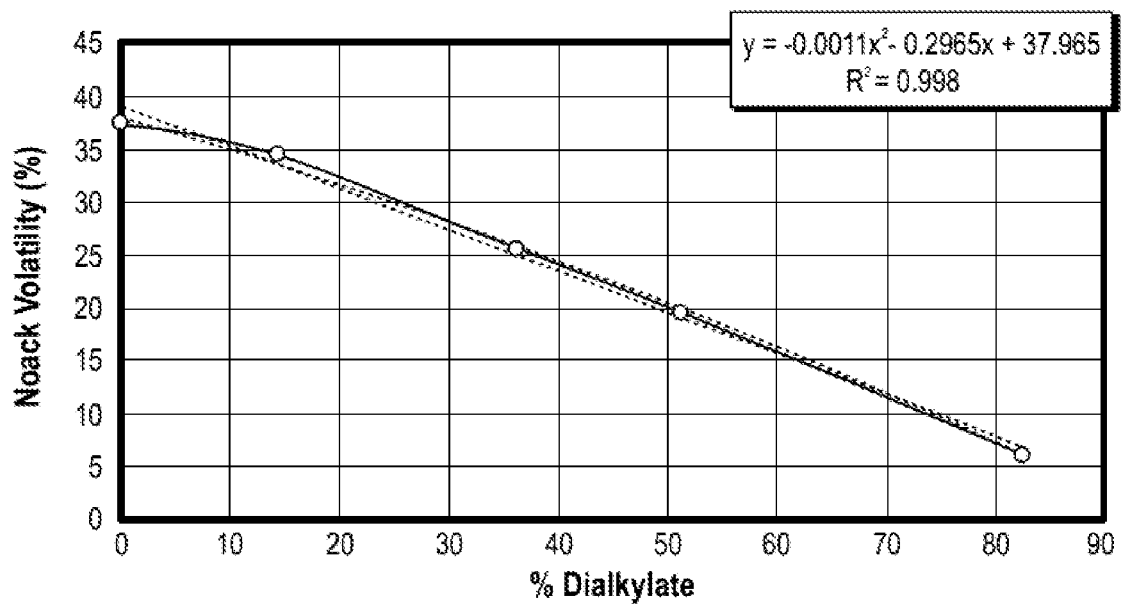
Figure 3A:
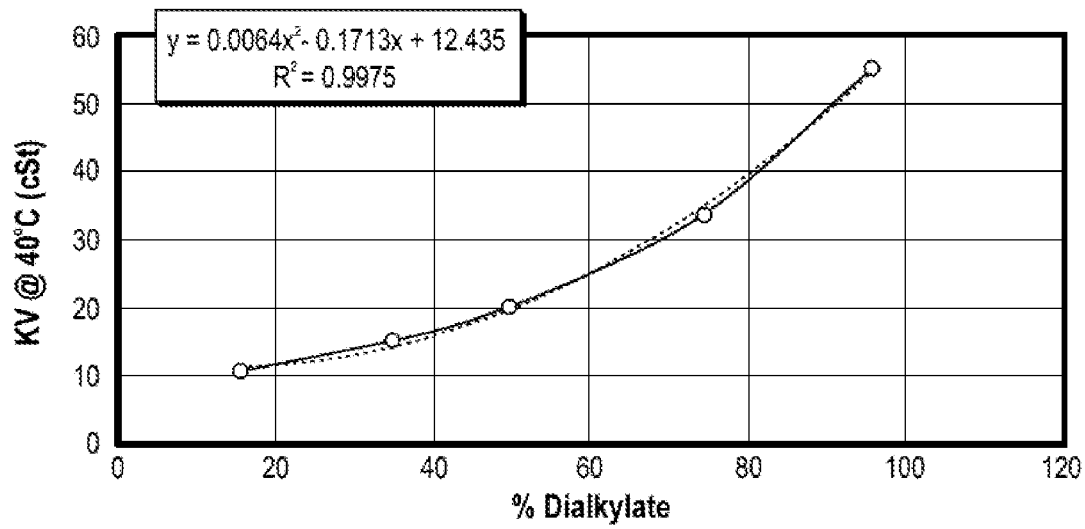
FIGS. 3A, 3B and 3C show plots of the kinematic viscosity at 40° C., the kinematic viscosity at 100° C., and the Noack volatility for blended $C_8$-alkylated naphthalene compositions versus the weight percentage of dialkylated naphthalenes present.
Figure 3B:
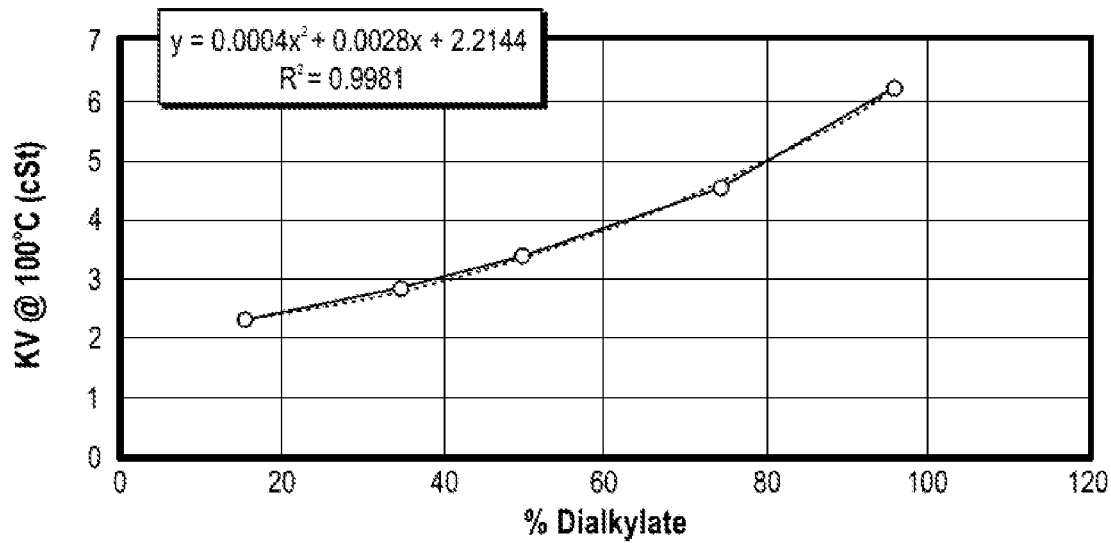
Figure 3C:
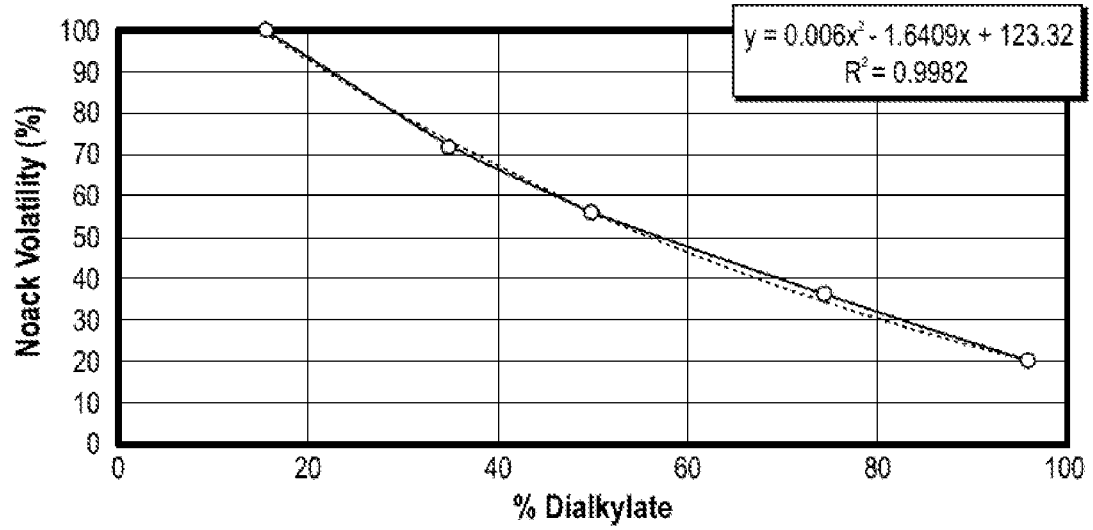

The kinematic viscosity values and the Noack volatility values for each class of alkylated naphthalene ($C_{16}$, $C_{12}$ or $C_8$ modified alkylated naphthalene composition) were plotted against the weight percentage of dialkylated naphthalenes present, and least squares fitting of the data was performed. FIGS. 1A, 1B and 1C show plots of the kinematic viscosity at 40° C., the kinematic viscosity at 100° C., and the Noack volatility for blended $C_{16}$-alkylated naphthalene compositions versus the weight percentage of dialkylated naphthalenes present. A polynomial regression function fitting the data is displayed on each plot. The kinematic viscosity plots may also be fit with an exponential regression function, and the Noack volatility may be alternately fit with a linear regression function. FIGS. 2A, 2B and 2C show corresponding plots for blended $C_{12}$-alkylated naphthalenes, and FIGS. 3A, 3B and 3C show corresponding plots for $C_8$-alkylated naphthalenes.

Figure 1D:
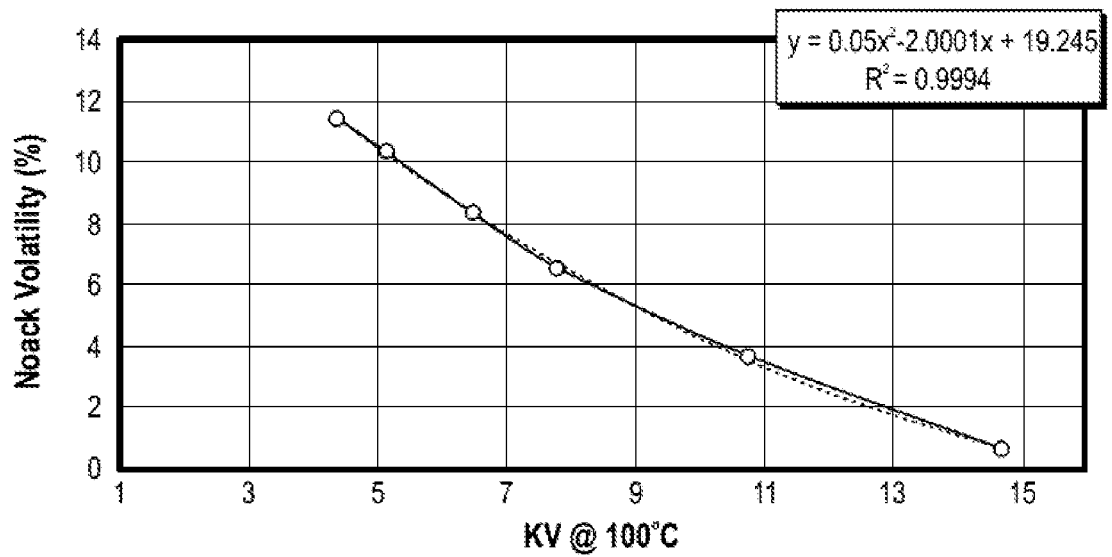
FIG. 1D shows a plot of Noack volatility versus kinematic viscosity at 100° C. for blended $C_{16}$-alkylated naphthalene compositions.
Figure 2D:
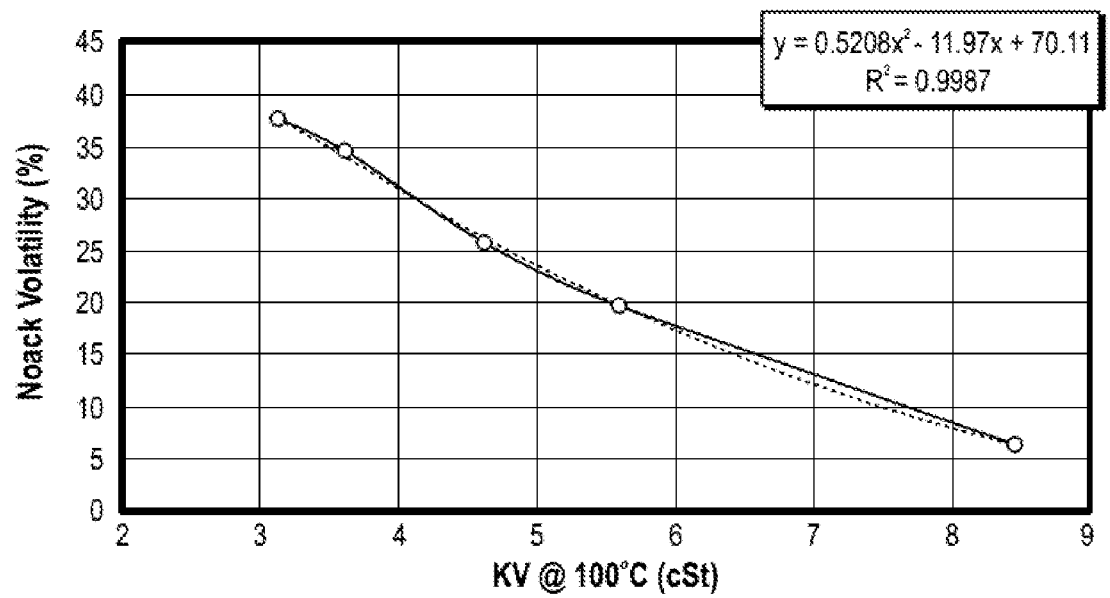
FIG. 2D shows a plot of Noack volatility versus kinematic viscosity at 100° C. for blended $C_{12}$-alkylated naphthalene compositions.
Figure 3D:
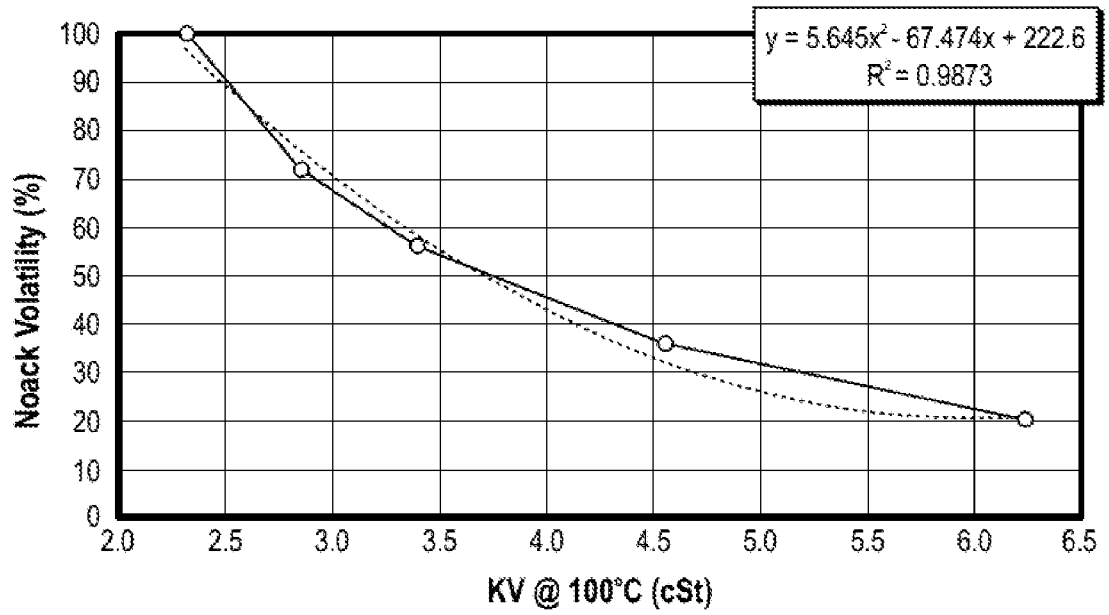
FIG. 3D shows a plot of Noack volatility versus kinematic viscosity at 100° C. for blended $C_8$-alkylated naphthalene compositions.

The corresponding relationship of Noack volatility to kinematic viscosity at 100° C. was also plotted for each type of modified alkylated naphthalene composition. FIG. 1D shows a plot of Noack volatility versus kinematic viscosity (100° C.) for blended $C_{16}$-alkylated naphthalene compositions. FIGS. 2D and 3D show corresponding plots for blended $C_{12}$-alkylated naphthalene compositions and $C_8$-alkylated naphthalene compositions, respectively. A polynomial regression function fitting the data is displayed on each plot. The $C_8$ data may also be fit with an exponential regression function.

Figure 4:
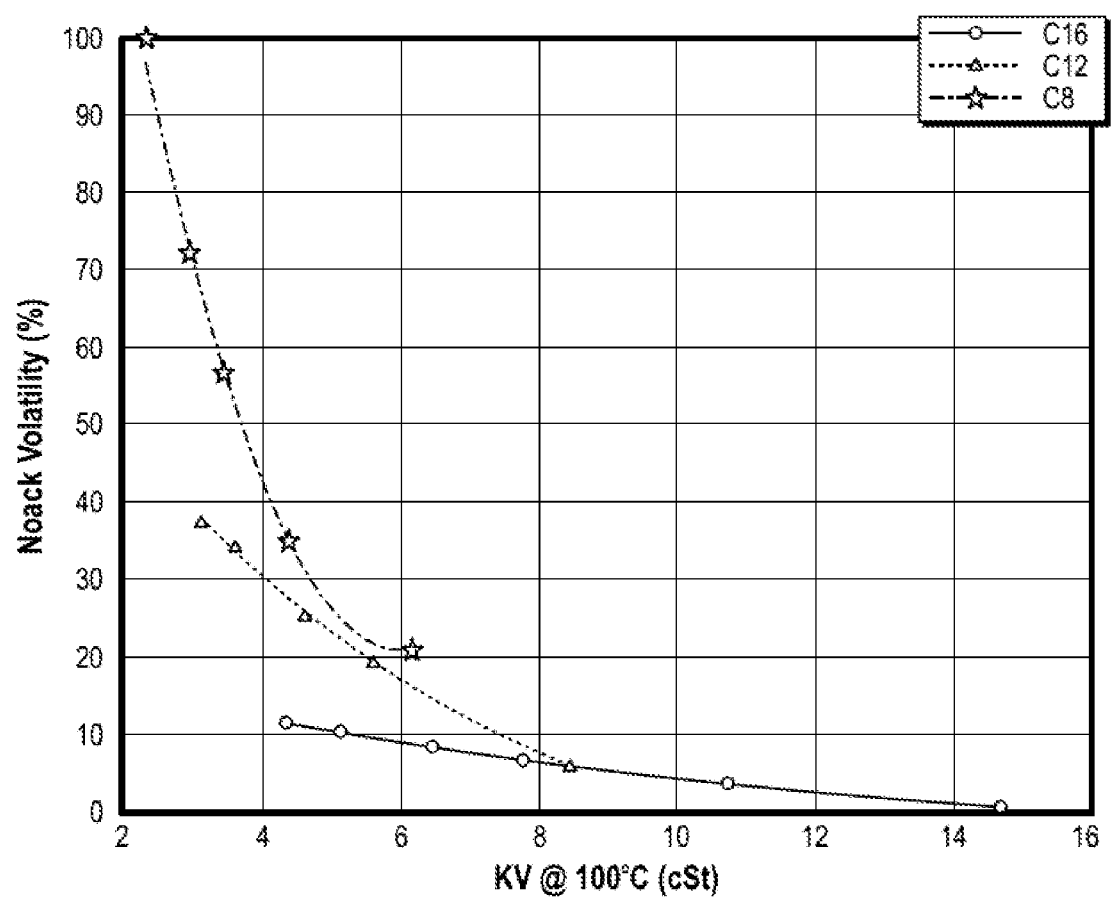
FIG. 4 shows an aggregate plot of the Noack volatility versus kinematic viscosity data from FIGS. 1D, 2D and 3D.

FIG. 4 shows an aggregate plot of the Noack volatility versus kinematic viscosity data from FIGS. 1D, 2D and 3D. By consulting FIG. 4 or a similar plot for other modified alkylated naphthalene compositions having an alkyl group with a different chain length, one may determine whether an alkylated naphthalene having an alkyl group with a given number of carbon atoms may afford a desired Noack volatility and/or kinematic viscosity. Once a modified alkylated naphthalene composition having an alkyl group of a given size is chosen, one may further determine a predicted Noack volatility when the monoalkylated naphthalenes and dialkylated naphthalenes are blended at a ratio sufficient to afford a targeted kinematic viscosity value. Conversely, one may determine a predicted kinematic viscosity when the monoalkylated naphthalenes and dialkylated naphthalenes are blended at a ratio sufficient to afford a targeted Noack volatility. Further discussion of these concepts is provided in the following examples.

Example 2: In this example, the data of Example 1 was used to select an alkylated naphthalene composition with a specified alkyl group carbon chain length and a blending ratio of monoalkylated naphthalenes to dialkylated naphthalenes needed to produce a targeted kinematic viscosity at 100° C. In particular, the goal of this example was to determine a blending ratio of monoalkylated naphthalenes to dialkylated naphthalenes having a specified alkyl group carbon chain length needed to match the kinematic viscosity at 100° C. for a mixture of $C_{14}$-alkylated naphthalene compounds obtained via a direct synthesis. Table 6 below summarizes the lubricant properties of the mixture of $C_{14}$-alkylated naphthalene compounds whose kinematic viscosity at 100° C. is to be matched in this example.

TABLE 6

| Kinematic Viscosity at 40° C. (cSt) | 115.5 |
| Kinematic Viscosity at 100° C. (cSt) | 13.1 |
| Viscosity Index | 107 |
| Noack Volatility (%) | 4.29 |

Referring to FIG. 4, it can be seen that only the $C_{16}$ alkylated naphthalene Noack volatility versus kinematic viscosity curve contains a point near the targeted kinematic viscosity at 100° C. of 13.1 cSt. The $C_{12}$ and $C_8$ alkylated naphthalene compositions do not reach a kinematic viscosity this high. Stated differently, the polynomial regression functions for $C_{12}$ and $C_8$ alkylated naphthalene compositions do not have positive root solutions when a kinematic viscosity value of 13.1 cSt is substituted for variable y. Substituting a value of 13.1 cSt for variable y in the regression function for the $C_{16}$ alkylated naphthalene compositions leads to a positive root solution for variable x of 87.8%. Thus, a $C_{16}$ modified alkylated naphthalene composition containing 12.2 wt. % monoalkylated naphthalenes and 87.8 wt. % dialkylated naphthalenes may afford the targeted kinematic viscosity. Taking the dialkylated naphthalene content of 87.8% and substituting for variable x in the corresponding polynomial regression function for Noack volatility (FIG. 1C), a predicted value of 2.04% results for the Noack volatility.

Testing of whether the predicted values were met was then conducted. A mixture of $C_{16}$-alkylated naphthalene compounds was synthesized under the conditions described above. The mixture contained approximately 90 wt. % monoalkylated naphthalenes and approximately 10 wt. % dialkylated naphthalenes. After fractional distillation, the overhead fraction from this mixture contained 92.5 wt. % monoalkylated naphthalenes and 7.5 wt. % dialkylated naphthalenes, and the bottoms fraction contained 0.1 wt. % monoalkylated naphthalenes and 99.9 wt. % dialkylated naphthalenes. The overhead fraction and the bottoms fraction were then recombined in amounts sufficient to produce a $C_{16}$ modified alkylated naphthalene composition comprising 13.0 wt. % monoalkylated naphthalenes and 87.0 wt. % dialkylated naphthalenes, a ratio close to that predicted to produce the targeted kinematic viscosity value at 100° C.

Table 7 below summarizes the lubricant properties of the mixture of $C_{14}$-alkylated naphthalene compounds, the predicted lubricant properties of the $C_{16}$ modified alkylated naphthalene composition, and the actual lubricant properties of the $C_{16}$ modified alkylated naphthalene composition formulated as above. The predicted properties were determined by inputting into an appropriate regression function the weight percent of dialkylated naphthalenes needed to afford the targeted kinematic viscosity at 100° C. of 13.1 cSt.

TABLE 7

|  | Mixture of $C_{14}$-alkylated naphthalene compounds | Predicted Properties of Blend | Measured Properties of Blend |
| --- | --- | --- | --- |
| Kinematic Viscosity at 40° C. (cSt) | 115.5 | 114 | 109.6 |
| Kinematic Viscosity at 100° C. (cSt) | 13.1 | 13.1 | 12.5 |

TABLE 7-continued

|  | Mixture of $C_{14}$-alkylated naphthalene compounds | Predicted Properties of Blend | Measured Properties of Blend |
| --- | --- | --- | --- |
| Viscosity Index | 107 | 100 | 106 |
| Noack Volatility (%) | 4.29 | 2.04 | 2.2 |

As shown, the $C_{16}$ modified alkylated naphthalene composition had lubricant properties that were close to those predicted. At least a portion of the variance may result from the slight compositional difference between the predicted ratio of monoalkylated naphthalenes to dialkylated naphthalenes compared to that actually formulated and tested. Somewhat surprisingly, lubricant properties for the blend were advantageous compared to those of the mixture of $C_{14}$-alkylated naphthalene compounds, since both a lower kinematic viscosity and a lower Noack volatility resulted.

Example 3: Example 2 was repeated, except the goal of this example was to determine a blending ratio of monoalkylated naphthalenes to dialkylated naphthalenes needed to match the Noack volatility for the mixture of $C_{14}$-alkylated naphthalene compounds (4.29%). Again, the $C_{16}$ modified alkylated naphthalene compositions provided the best opportunity for matching the Noack volatility of the mixture of $C_{14}$-alkylated naphthalene compounds. In this case, the predicted amount of dialkylated naphthalenes needed to afford the targeted Noack volatility value was 70.4 wt. % (29.6 wt. % monoalkylated naphthalenes to 70.4 wt. % dialkylated naphthalenes). Substituting the calculated weight percentage of dialkylated naphthalenes into the regression function for kinematic viscosity at 100° C., a predicted kinematic viscosity value of 10.4 cSt resulted.

The overhead fraction and the bottoms fraction from Example 2 were recombined in amounts sufficient to produce a $C_{16}$ modified alkylated naphthalene composition comprising 30.0 wt. % monoalkylated naphthalenes and 70.0 wt. % dialkylated naphthalenes, a ratio close to that predicted to produce the targeted Noack volatility.

Table 8 below summarizes the lubricant properties of the mixture of $C_{14}$-alkylated naphthalene compounds, the predicted lubricant properties of the $C_{16}$ modified alkylated naphthalene composition, and the actual lubricant properties of the $C_{16}$ modified alkylated naphthalene composition formulated as above. The predicted values were determined by inputting into an appropriate regression equation the weight percent of dialkylated naphthalenes needed to afford the targeted Noack volatility of 4.29%.

TABLE 8

|  | Mixture of $C_{14}$-alkylated naphthalene compounds | Predicted Properties of Blend | Measured Properties of Blend |
| --- | --- | --- | --- |
| Kinematic Viscosity at 40° C. (cSt) | 115.5 | 84.2 | 81.0 |
| Kinematic Viscosity at 100° C. (cSt) | 13.1 | 10.4 | 10.2 |
| Viscosity Index | 107 | 106 | 106 |
| Noack Volatility (%) | 4.29 | 4.50 | 4.29 |

As shown, the $C_{16}$ modified alkylated naphthalene composition had lubricant properties that were fairly close to those predicted. At least a portion of the variance may result from the slight compositional difference between the predicted ratio of monoalkylated naphthalenes to dialkylated naphthalenes compared to that actually formulated and tested. Somewhat surprisingly, lubricant properties for the blend were advantageous compared to those of the mixture of $C_{14}$-alkylated naphthalene compounds, since a lower kinematic viscosity was realized at a comparable Noack volatility value.

Referring again to FIGS. 4 and 2C, it can be seen that $C_{12}$ modified alkylated naphthalene compositions would also be capable of producing a Noack volatility of 4.29% at a dialkylated naphthalene content somewhere above 83 wt. % (outside of the calibration range), thereby leading to a corresponding kinematic viscosity at 100° C. above 8.5 cSt (also outside of calibration range). Since the required weight percentage of dialkylated naphthalenes exceeds that obtained in the bottoms fraction, matching the Noack volatility with a $C_{12}$ modified alkylated naphthalene composition may be disadvantaged compared to using a $C_{16}$ modified alkylated naphthalene composition. It should be appreciated, however, that enrichment of the $C_{12}$ bottoms fraction may be realized through redistillation to remove at least a portion of the residual $C_{12}$ monoalkylated naphthalenes to afford a bottoms fraction with a sufficiently high $C_{12}$-dialkylated naphthalene content for matching the Noack volatility of the mixture of $C_{14}$-alkylated naphthalene compounds. Alternately, the initial fractional distillation may be conducted such that a higher dialkylated naphthalene content results in the bottoms fraction. Matching of the kinematic viscosity may be realized similarly with alkylated naphthalenes comprising an alkyl group with a different number of carbon atoms.

Example 4: A mixture of $C_{16}$-alkylated naphthalene compounds was synthesized under the conditions described above. The mixture contained approximately 90 wt. % monoalkylated naphthalenes and approximately 10 wt. % dialkylated naphthalenes. This type of product distribution is characteristic of many as-produced alkylated naphthalene compositions. After fractional distillation, the overhead fraction contained 99.8 wt. % monoalkylated naphthalenes and 0.2 wt. % dialkylated naphthalenes, and the bottoms fraction contained 2.2 wt. % monoalkylated naphthalenes and 97.8 wt. % dialkylated naphthalenes. The overhead fraction and the bottoms fraction were recombined in varying amounts to produce $C_{16}$ modified alkylated naphthalene compositions ranging from 88.2-99.6 wt. % monoalkylated naphthalenes and 11.7-0.4 wt. % dialkylated naphthalenes.

The following lubricant properties of the $C_{16}$ modified alkylated naphthalene compositions produced in this example were measured: Group 1) kinematic viscosity at 40° C. and 100° C., viscosity index, CCS viscosity at −25° C., −30° C. and −35° C., and Group 2) Brookfield viscosity at −26° C. and −40° C., MRV at −35° C. and −40° C., and kinematic viscosity at −40° C. Table 9 summarizes the lubricant property testing data and testing procedures used.

TABLE 9

| | Method | 0.3 Wt. % Di-alkylate | 7.5 Wt. % Di-alkylate | 1 Wt. % Di-alkylate | 3 Wt. % Di-alkylate |
|---|---|---|---|---|---|
| Monoalkylate (wt. %) | GC | 99.6 | 92.41 | 98.82 | 96.88 |
| Dialkylate (wt. %) | GC | 0.27 | 7.5 | 1.02 | 2.99 |
| Color, Pt-Co | ASTM D1500 | 0.5 | 0.6 | 0.6 | 0.6 |

TABLE 9-continued

| CCS Viscosity @ −25° C. (cP) | ASTM D5293 | 2543 | 3097 | 2579 | 2682 |
|---|---|---|---|---|---|
| CCS Viscosity @ −30° C. (cP) | ASTM D5293 | 4890 | 5859 | 4926 | 5213 |
| CCS Viscosity @ −35° C. (cP) | ASTM D5293 | 9887 | 11941 | 9955 | 10544 |
| Brookfield Viscosity @ −40° C. (cP) | ASTM D2983 | 19980 | 41700 | 22260 | 23430 |
| Brookfield Viscosity @ −26° C. (cP) | ASTM D2983 | 3210 | 3963 | 3249 | 3408 |
| Pour Point (° C.) | ASTM D5950 | −45 | −39 | −42 | −42 |
| Noack Volatility (%) | ASTM D5800 | 11.47 | 10.72 | 11.68 | 11.23 |
| Kinematic Viscosity @ 100° C. (cSt) | ASTM D445 | 4.36 | 4.76 | 4.39 | 4.49 |
| Kinematic Viscosity @ 40° C. (cSt) | ASTM D445 | 25 | 28.34 | 25.31 | 26.21 |
| Viscosity Index | ASTM D2270 | 67 | 78 | 67 | 70 |
| RPVOT Neat (min) | ASTM D2272 | 259 | 327 | 244 | 232 |
| MRV Viscosity @ −35° C. (cP) | ASTM D4684 | 9322 | 11360 | 9786 | 10581 |
| MRV Viscosity @ −40° C. (cP) | ASTM D4684 | 5332 | 28000 | 22495 | 23935 |
| Kinematic Viscosity @ −40° C. (cSt) | ASTM D445 | 23106 | TVTM* | 23413 | 24770 |

| | Method | 5 Wt. % Di-alkylate | 6.5 Wt. % Di-alkylate | 10 Wt. % Di-alkylate | 12 Wt. % Di-alkylate |
|---|---|---|---|---|---|
| Monoalkylate (wt. %) | GC | 94.92 | 93.45 | 90.05 | 88.16 |
| Dialkylate (wt. %) | GC | 4.96 | 6.45 | 9.85 | 11.74 |
| Color, Pt-Co | ASTM D1500 | 0.6 | 0.6 | 0.7 | 0.7 |
| CCS Viscosity @ −25° C. (cP) | ASTM D5293 | 2929 | 3122 | 3362 | 3480 |
| CCS Viscosity @ −30° C. (cP) | ASTM D5293 | 5532 | 5905 | 6388 | 6631 |
| CCS Viscosity @ −35° C. (cP) | ASTM D5293 | 11237 | 11993 | 13031 | 13576 |
| Brookfield Viscosity @ −40° C. (cP) | ASTM D2983 | 26070 | 30800 | 140200 | 318000 |
| Brookfield Viscosity @ −26° C. (cP) | ASTM D2983 | 3450 | 3753 | 4011 | 4524 |
| Pour Point (° C.) | ASTM D5950 | −42 | −39 | −39 | −39 |
| Noack Volatility (%) | ASTM D5800 | 11.13 | 10.91 | 10.63 | 10.8 |
| Kinematic Viscosity @ 100° C. (cSt) | ASTM D445 | 4.61 | 4.69 | 4.88 | 4.99 |
| Kinematic Viscosity @ 40° C. (cSt) | ASTM D445 | 27.13 | 27.79 | 29.34 | 30.2 |
| Viscosity Index | ASTM D2270 | 74 | 76 | 81 | 84 |
| RPVOT Neat (min) | ASTM D2272 | 284 | 296 | 224 | 254 |
| MRV Viscosity @ −35° C. (cP) | ASTM D4684 | 10896 | 11460 | 12452 | 12677 |
| MRV Viscosity @ −40° C. (cP) | ASTM D4684 | 25728 | 29675 | 36924 | 52160 |

TABLE 9-continued

| Kinematic Viscosity @ -40° C. (cSt) | ASTM D445 | 26403 | TVTM* | TVTM* | TVTM* |

TVTM = too viscous to measure
CCS = cold cranking simulator, which simulates the viscosity of a lubricant in crankshaft bearings during engine startup on a cold day.
MRV = mini-rotary viscometer, which measures the pumpability of a lubricant at low temperatures.
RPVOT = rotary pressure vessel oxidation test.

Figure 5:
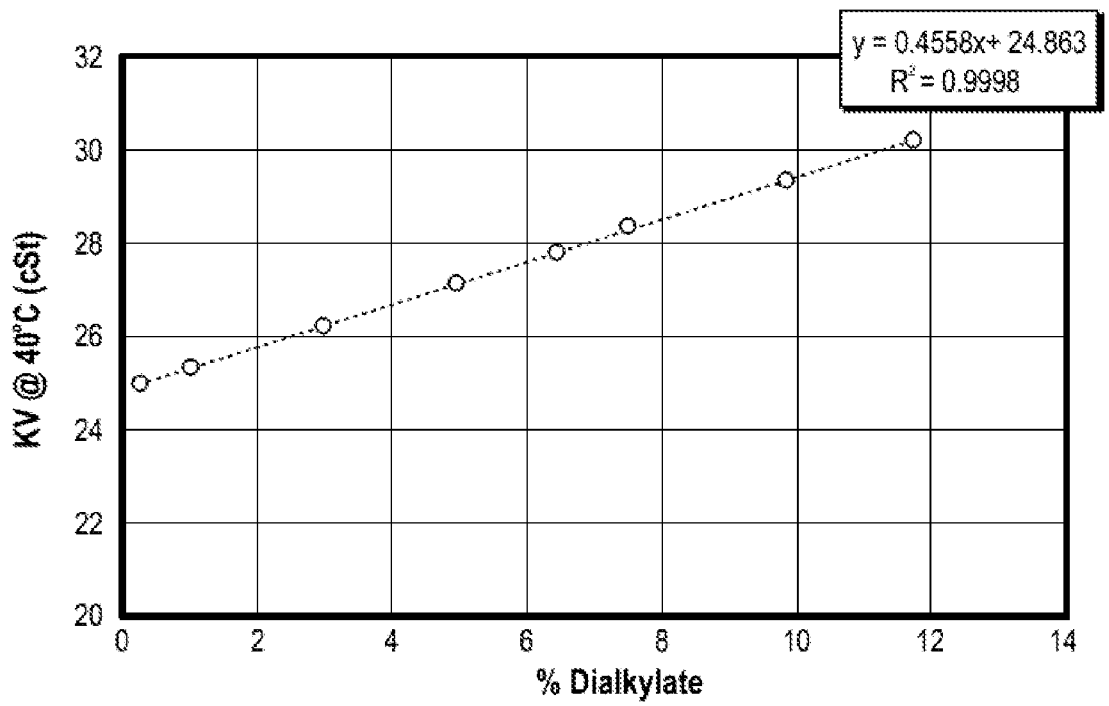
FIG. 5 shows a plot of kinematic viscosity at 40° C. versus the weight percentage of $C_{16}$ dialkylated naphthalenes (0.4-11.7 wt. %) in the modified alkylated naphthalene compositions of Example 4.
Figure 6:
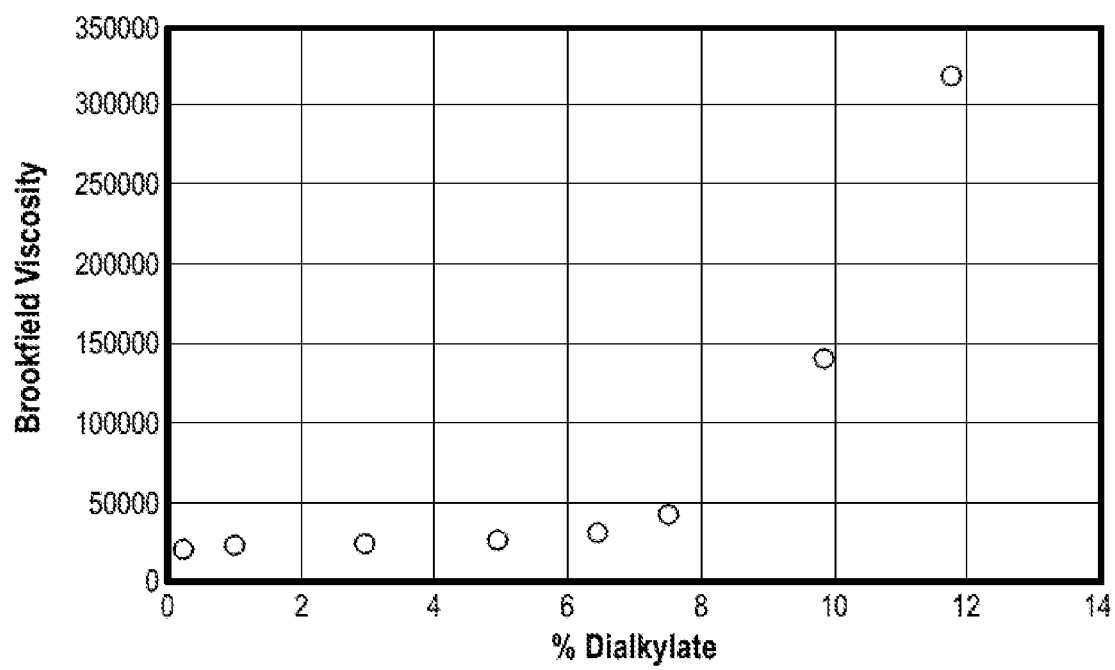
FIG. 6 shows a plot of Brookfield viscosity at −40° C. versus the weight percentage of $C_{16}$ dialkylated naphthalenes (0.4-11.7 wt. %) in the modified alkylated naphthalene compositions of Example 4.

The lubricant properties in the first group varied linearly over the tested weight percentage range of dialkylated naphthalenes. The lubricant properties in the second group varied non-linearly over the tested weight percentage range of dialkylated naphthalenes. As an illustrative example of the linear variation within the tested weight percentage range for dialkylated naphthalenes, FIG. 5 shows a plot of kinematic viscosity at 40° C. versus the weight percentage of $C_{16}$ dialkylated naphthalenes (0.4-11.7 wt. %). As an illustrative example of the non-linear variation within the tested weight percentage range for dialkylated naphthalenes, FIG. 6 shows a plot of Brookfield viscosity at -40° C. versus the weight percentage of $C_{16}$ dialkylated naphthalenes (0.4-11.7 wt. %).

As shown, the non-linear variance in the Brookfield viscosity increased rapidly above about 10 wt. % dialkylated naphthalene, the typical best-case weight percentage produced by direct alkylation of naphthalene. Below about 8 wt. % dialkylated naphthalenes, the Brookfield viscosity was much lower than would be predicted based upon the viscosity value observed at about 10 wt. % dialkylated naphthalenes. Given the very steep increase between the viscosity value for 10 wt. % dialkylated naphthalenes and 11.7 wt. % dialkylated naphthalenes, weight percentages commonly observed in as-obtained alkylated naphthalene compositions, one would not have predicted the much lower Brookfield viscosity values observed below about 8 wt. % dialkylated naphthalenes, weight percentages not commonly observed in as-obtained alkylated naphthalene compositions. It should be noted that the data in FIG. 6 below about 8 wt. % dialkylated naphthalenes may be effectively fit with a linear least squares regression function. In addition, the data shown in FIG. 5 corresponds to a portion of the data shown in FIG. 1A, which is best fit with a polynomial regression function over the entire range of dialkylated naphthalene weight percentages. The data in FIG. 5 may also be effectively fit with a polynomial regression function or an exponential regression function. Accordingly, the linear least squares fit in FIG. 5 should not be considered limiting with respect to the scope of the present disclosure, nor should the particular fitting protocol used for any other set of data herein. Thus, by combining an overhead fraction and a bottoms fraction comprising predominantly monoalkylated naphthalenes and dialkylated naphthalenes, respectively, modified alkylated naphthalene compositions having unexpectedly good low-temperature lubricant properties may be obtained. Alkylated naphthalene compositions having about 3 wt. % dialkylated naphthalenes or lower may be particularly advantageous with respect to their low-temperature lubricant properties.

Example 5: In this example, fully formulated lubricant compositions were prepared with a $C_{16}$ modified alkylated naphthalene composition containing greater than 97 wt. % monoalkylated naphthalenes and less than 3 wt. % dialkylated naphthalenes (Example 4), in which a conventional alkylated naphthalene lubricant base stock was replaced in the formulated lubricant compositions. The conventional alkylated naphthalene lubricant base stock used in this example was a mixture of alkylated naphthalene compounds (93 wt. % monoalkylated naphthalenes and 7 wt. % dialkylated naphthalenes) having a kinematic viscosity at 100° C. of 5 cSt.

Table 10 summarizes various properties of automotive gear oil (AGO) 90 formulated from a conventional alkylated naphthalene lubricant base stock (Formulation A) against those formulated from a $C_{16}$ modified alkylated naphthalene composition containing greater than 97 wt. % monoalkylated naphthalenes and less than 3 wt. % dialkylated naphthalenes (Formulation B).

TABLE 10

| Component (KV @ 100° C.) | Formulation A (wt. %) | Formulation B (wt. %) |
|---|---|---|
| EHC 50 GRP II (5.4 cSt) | 50.8 | 50.24 |
| SPECTRASYN ELITE 150 (157 cSt) | 31.7 | 32.26 |
| 93 wt. % monoalkylated naphthalenes/7 wt. % dialkylated naphthalenes (4.7 cSt) | 10.0 | — |
| 97 wt. % monoalkylated naphthalenes/3 wt. % dialkylated naphthalenes (4.3 cSt) | — | 10.0 |
| HITEC 385 (15.93 cSt) | 7.5 | 7.5 |
| Total: | 100 | 100 |
| Lubricant Properties | | |
| KV @ 40° C., cSt — ASTM D445 | 99.98 | 99.9 |
| KV @ 100° C., cSt — ASTM D445 | 14.75 | 14.96 |
| VI — ASTM D2270 | 154 | 157 |
| Pour Point, ° C. — ASTM D5950 | -24 | -24 |
| Brookfield @ -26° C., cP — ASTM D2983 | 19,560 | 25,050 |
| Brookfield @ -40° C., cP — ASTM D2983 | 1,620,000 | 372,000 |
| Appearance — visual | B&C | B&C |
| Foam Seq I — ASTM D892 | 550/20 | 620/270 |
| Foam Seq II | 55/0 | 80/0 |
| Foam Seq III | 390/5 | 560/170 |
| RPVOT, minutes — ASTM D2272 | 95 | 151 |
| 4-Ball Wear, mm — ASTM D4172 | 0.74 | 0.75 |
| Taper Rolling Bearing (CEC-L45-A-99) — Relative Vis loss, % at 20 hrs | 0.6 | 0.1 |
| Relative Vis loss, % at 100 hrs | 0.5 | 1.5 |

As shown, the Brookfield viscosity at -40° C. was considerably lower for the formulated lubricant compositions when the incorporated alkylated naphthalenes contained greater than 97 wt. % monoalkylated naphthalenes and less than 3 wt. % dialkylated naphthalenes. The considerably decreased viscosity is particularly surprising given the relatively low loading of alkylated naphthalenes in the formulated lubricant compositions and the slight difference in dialkylated naphthalene content between the two formulated lubricant compositions. Thus, the formulated AGO compositions illustrate the low-temperature viscosity issues produced by excessive amounts of dialkylated naphthalenes and the surprising improvements afforded by decreasing the dialkylated naphthalene content.

Table 11 summarizes various properties of industrial gear oil (IGO) ISO VG 320 formulated from a conventional alkylated naphthalene lubricant base stock (Formulation C) against those formulated from a $C_{16}$ modified alkylated naphthalene composition containing greater than 97 wt. % monoalkylated naphthalenes and less than 3 wt. % dialkylated naphthalenes (Formulation D).

TABLE 11

| Component (KV @ 40° C.) | | Formulation C (wt. %) | Formulation D (wt. %) |
|---|---|---|---|
| SPECTRASYN 6 (31 cSt) | | 25.42 | 24.75 |
| SPECTRASYN ELITE 150 (1645 cSt) | | 63.08 | 63.75 |
| 93 wt. % monoalkylated naphthalene/7 wt. % dialkylated naphthalene (28.4 cSt) | | 10.0 | — |
| 97 wt. % monoalkylated naphthalene/3 wt. % dialkylated naphthalene (26.2 cSt) | | — | 10.0 |
| ELCO 393D (42 cSt) | | 1.5 | 1.5 |
| Total: | | 100 | 100 |
| Lubricant Properties | | | |
| KV @ 40° C., cSt | ASTM D445 | 318.8 | 319.4 |
| KV @ 100° C., cSt | ASTM D445 | 40.69 | 40.99 |
| VI | ASTM D2270 | 182 | 183 |
| Pour Point, ° C. | ASTM D5950 | −54 | −54 |
| Brookfield @ −26° C., cP | ASTM D2983 | 33,960 | 38,200 |
| Brookfield @ −40° C., cP | ASTM D2983 | 295,000 | 217,600 |
| Appearance | visual | Cloudy | Hazy |
| Foam Seq I | ASTM D892 | 650/285 | 640/420 |
| Foam Seq II | | 60/0 | 80/0 |
| Foam Seq III | | 560/100 | 600/370 |
| RPVOT, minutes | ASTM D2272 | 368 | 390 |
| 4-Ball Wear, mm | ASTM D4172 | 0.50 | 0.55 |
| TaperRolling Bearing (CEC-L45-A-99) | Relative Vis loss, % at 20 hrs | 0.5 | 0.4 |
| | Relative Vis loss, % at 100 hrs | −1.6 | 0.2 |

Again, the formulated lubricant composition containing low amounts of dialkyalted naphthalenes (Formulation D) exhibited a considerably lower Brookfield viscosity at −40° C.

5W30 and 10W30 motor oils may also be formulated using a $C_{16}$ modified alkylated naphthalene composition containing greater than 97 wt. % monoalkylated naphthalenes and less than 3 wt. % dialkylated naphthalenes. Table 12 below compares the lubricant properties of conventional 5W30 and 10W30 motor oils, 5W30 and 10W30 motor oils formulated with a conventional alkylated naphthalene base stock comprising a mixture of alkylated naphthalene compounds (93 wt. % monoalkylated naphthalenes and 7 wt. % dialkylated naphthalenes), and modified 5W30 and 10W30 motor oils formulated with a $C_{16}$ modified alkylated naphthalene composition containing greater than 97 wt. % monoalkylated naphthalenes and less than 3 wt. % dialkylated naphthalenes.

TABLE 12

| Base Lubricant (KV @ 100° C., cSt) | 5W30 | Modified 5W30 | Modified 5W30 with low dialkylated naphthalenes | 10W30 | Modified 10W30 | Modified 10W30 with low dialkylated naphthalenes |
|---|---|---|---|---|---|---|
| YUBABASE 4 (4.237) | — | — | — | 70.70 | 60.70 | 60.50 |
| SPECTRASYN 4 (4.144) | 70.00 | 60.00 | 60.00 | — | — | — |
| 93 wt % monoalkylated naphthalene/7 wt. % dialkylated naphthalene (4.7 cSt) | — | 10.00 | — | — | 10.00 | — |
| 97 wt. % monoalkylated naphthalene/3 wt. % dialkylated naphthalene (4.3 cSt) | — | — | 10.00 | — | — | 10.00 |
| INFINEUM P6003 (146.1) | 12.00 | 12.00 | 12.00 | 12.00 | 12.00 | 12.00 |
| Total (%) | 100.00 | 100.00 | 100.00 | 100.00 | 100.00 | 100.00 |
| Luricant Properties | | | | | | |
| KV @ 40° C. (cSt) | 60.78 | 61.49 | 60.49 | 60.31 | 61.89 | 61.31 |
| KV @ 100° C. (cSt) | 10.56 | 10.62 | 10.51 | 10.39 | 10.55 | 10.53 |
| VI | 165 | 164 | 164 | 162 | 161 | 162 |
| Pour Point (° C.) | −60 | −66 | −63 | −24 | −30 | −27 |
| CCS @ −25° C. (cP) | — | — | — | 3,769 | 3,835 | 3,975 |
| CCS @ −30° C. (cP) | 4,834 | 4,886 | 5,166 | 6,769 | — | — |
| MRV @ −30° C. (cP) | 5,014 | — | — | 22,294 | 13,369 | 12,300 |
| MRV @ −35° C. (cP) | 8,723 | 10,782 | 9,700 | 36,075 | — | — |
| HTHS @ 150° C. (cP) | 3.365 | 3.395 | 3.359 | 3.373 | 3.419 | 3.455 |

TABLE 12-continued

| Base Lubricant (KV @ 100° C., cSt) | 5W30 | Modified 5W30 | Modified 5W30 with low dialkylated naphthalenes | 10W30 | Modified 10W30 | Modified 10W30 with low dialkylated naphthalenes |
|---|---|---|---|---|---|---|
| Noack volatility @ 250° C. (wt. % loss) | 9.8 | 9.2 | 9.6 | 11.6 | 11.4 | 11.3 |

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is the following:

1. A method comprising:
providing a first alkylated naphthalene composition comprising at least one monoalkylated naphthalene and at least one dialkylated naphthalene;
obtaining a first fraction enriched in the at least one monoalkylated naphthalene of the first alkylated naphthalene and a second fraction enriched in the at least one dialkylated naphthalene of the first alkylated naphthalene; and
combining a portion of the first fraction with a portion of the second fraction to obtain a modified alkylated naphthalene composition differing in composition from the first alkylated naphthalene composition and having one or more lubricant properties differing from the first alkylated naphthalene composition.

2. The method of claim 1, wherein the first fraction and the second fraction are obtained by fractional distillation of the first alkylated naphthalene composition, and the first fraction comprises an overhead fraction of the fractional distillation and the second fraction comprises a bottoms fraction of the fractional distillation.

3. The method of claim 1, wherein providing the alkylated naphthalene composition comprises reacting an olefin, an alkyl halide, an alkanol, or any combination thereof with naphthalene under acid-catalyzed reaction conditions.

4. The method of claim 1, wherein the at least one monoalkylated naphthalene and the at least one dialkylated naphthalene comprise a $C_6$-$C_{20}$ alkyl group.

5. The method of claim 3, wherein the olefin comprises an alpha olefin.

6. The method of claim 1, wherein the first fraction comprises about 95 wt. % or greater of the at least one monoalkylated naphthalene and the second fraction comprises about 80 wt. % or greater of the at least one dialkylated naphthalene.

7. The method of claim 1, wherein the first fraction comprises about 99 wt. % or greater of the at least one monoalkylated naphthalene and the second fraction comprises about 90 wt. % or greater of the at least one dialkylated naphthalene.

8. The method of claim 1, further comprising:
    selecting a targeted value for one of the one or more lubricant properties; and
    determining an amount of the first fraction and an amount of the second fraction needed to provide a ratio of the at least one monoalkylated naphthalene to the at least one dialkylated naphthalene to produce the targeted value.

9. The method of claim 8, wherein the ratio of the at least one monoalkylated naphthalene to the at least one dialkylated naphthalene is determined from a calibration curve or a regression function.

* * * * *